United States Patent [19]

Buendia et al.

[11] 4,279,919

[45] Jul. 21, 1981

[54] NOVEL LACTONES OF CYCLOPENTANOLS

[75] Inventors: Jean Buendia, Le Perreux-sur-Marne; Michel Vivat, Lagny-sur-Marne, both of France

[73] Assignee: Roussel Uclaf, Paris, France

[21] Appl. No.: 131,053

[22] Filed: Mar. 17, 1980

Related U.S. Application Data

[63] Continuation-in-part of Ser. No. 36,877, May 8, 1979, Pat. No. 4,221,809, which is a continuation-in-part of Ser. No. 779,178, Mar. 18, 1977, abandoned.

[30] Foreign Application Priority Data

Mar. 19, 1976 [FR] France .............................. 76 08004
Oct. 28, 1978 [FR] France .............................. 78 30054

[51] Int. Cl.³ .................. A61K 31/365; C07D 305/14
[52] U.S. Cl. ................................. 424/279; 260/343.21
[58] Field of Search ................... 260/343.21; 542/426, 542/429; 424/279

[56] References Cited

U.S. PATENT DOCUMENTS 3,823,138  7/1974  Van Rheenen ............... 260/343.3 P
4,109,009  8/1978  Buendia et al. ...................... 424/305

OTHER PUBLICATIONS

Chem. Abstract, 5994z, vol. 89.
Buendia et al., Chem. Abst. 59708c, vol. 89.

Primary Examiner—Henry R. Jiles
Assistant Examiner—Jane T. Fan
Attorney, Agent, or Firm—Hammond & Littell, Weissenberger and Muserlian

[57] ABSTRACT

Novel lactones of the formula

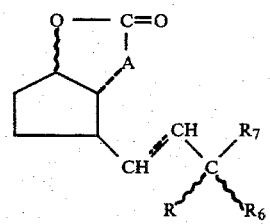

wherein the dotted line indicates the optional presence of a second bond, A is a single bond or —CH$_2$—CH$_2$—, R is selected from the group consisting of hydrogen, alkyl of 1 to 4 carbon atoms and alkenyl and alkynyl of 2 to 4 carbon atoms, R$_6$ is —OR$_A'$, R$_A'$ is selected from the group consisting of hydrogen, tetrahydropyranyl, alkyl of 1 to 3 carbon atoms and

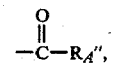

R$_A''$ is selected from the group consisting of alkyl of 1 to 3 carbon atoms optionally substituted with carboxyl and phenyl optionally substituted with a member of the group consisting of carboxyl, free hydroxyl, hydroxyl protected with an acyl of 2 to 4 carbon atoms and hydroxyl protected with an easily hydrolyzable group and R and R$_6$ together form a keto group, R$_7$ is —CH$_2$—)$_{m_A}$—CH$_3$, m$_A$ is 3,4,5 or 6 and R$_6$ and R$_7$ taken together form =CH—(CH$_2$)$_{n_A}$—CH$_3$, n$_A$ is 2,3,4 or 5 and the wavy lines indicate that the bonds are in one or the other of the possible configurations and when A is a simple bond, the bond between the cyclopentane ring and the oxygen is in the α-position having hypotensive activity and the wavy lines represent a paired configuration selected from the group consisting of α,β and β,α and mixtures thereof and novel processes and intermediates for their preparation.

6 Claims, No Drawings

NOVEL LACTONES OF CYCLOPENTANOLS

PRIOR APPLICATION

This application is a continuation-in-part of copending patent application Ser. No. 36,877 filed May 8, 1979, now U.S. Pat. No. 4,221,809, issued Sept. 9, 1980 which in turn is a continuation-in-part of our copending commonly assigned U.S. patent application Ser. No. 779,178 filed Mar. 18, 1977, now abandoned.

STATE OF THE ART

U.S. Pat. No. 3,823,138 describes certain prostaglandin compounds.

OBJECTS OF THE INVENTION

It is an object of the invention to provide the novel lactones of formula I' as well as novel processes for their preparation and novel intermediates formed therein.

It is another object of the invention to provide novel hypotensive compositions and to a novel method of relieving hypertension in warm-blooded animals.

These and other objects and advantages of the invention will become obvious from the following detailed description.

THE INVENTION

The novel cyclopentanol derivatives of the invention have the formula

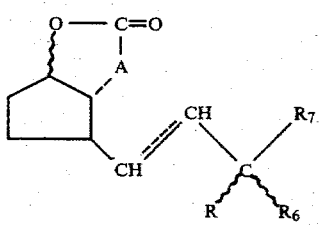

R' wherein the dotted line indicates the optional presence of a second bond, A is a simple bond or —CH$_2$—CH$_2$—, R is selected from the group consisting of hydrogen, alkyl of 1 to 4 carbon atoms and alkenyl and alkynyl of 2 to 4 carbon atoms, R$_6$ is —OR$_A$', R$_A$' is selected from the group consisting of hydrogen, tetrahydropyranyl, alkyl of 1 to 3 carbon atoms and

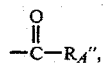

R$_A$'' is selected from the group consisting of alkyl of 1 to 3 carbon atoms optionally substituted with carboxyl and phenyl optionally substituted with a member of the group consisting of carboxyl, free hydroxyl, hydroxyl protected with an acyl of 2 to 4 carbon atoms and hydroxyl protected with an easily hydrolyzable group and R and R$_6$ together form a keto group, R$_7$ is —(CH$_2$)$_{mA}$—CH$_3$, m$_A$ is 3,4,5 or 6 and R$_6$ and R$_7$ taken together form =CH—(CH$_2$)$_{nA}$—CH$_3$, n$_A$ is 2,3,4 or 5 and the wavy lines indicate that the bonds are in one or the other of the possible configurations and when A is a simple bond, the bond between the cyclopentane ring and the oxygen is in the α-position.

Among the preferred compounds of the invention are those of the formula

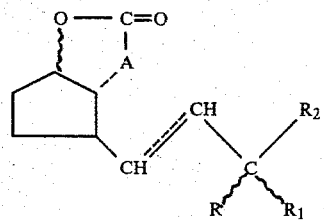

I wherein A and R have the above definitions, R$_1$ is —OR', R' is selected from the group consisting of hydrogen, tetrahydropyranyl, alkyl of 1 to 3 carbon atoms and

R'' is selected from the group consisting of alkyl of 1 to 3 carbon atoms and phenyl optionally substituted with carboxyl, R and R$_1$ together form a keto group, R$_2$ is (CH$_2$)$_m$—CH$_3$, m is 3,4 or 5 and R$_1$ and R$_2$ together form =CH—(CH$_2$)$_n$—CH$_3$ and n is 2,3 or 4 and the wavy lines indicate that the bonds are in one or the other of the possible configurations and when A is a simple bond, the bond between the cyclopentane ring and the oxygen is in the a-position.

Examples of R are hydrogen, methyl, ethyl, propyl, isopropyl, butyl isobutyl, tert.-butyl, vinyl, propenyl, butenyl, ethynyl or propargyl. Examples of R', R$_4$', R'' and R$_A$'' are methyl, ethyl, propyl or isopropyl. Examples of acyl to protect the hydroxyl on the phenyl are derived from alkanoic acids such as acetic acid, propionic acid, n-butyric acid or isobutyric acid. Examples of groups easily removable by hydrolysis are tetrahydropyranyl or tert.-butyl dimethylsilyl.

One preferred group of compounds of formula I are those where the dotted line is a second bond, A has the above definition, R is hydrogen or alkynyl or alkenyl of 2 to 3 carbon atoms, R$_1$ is OR', R' is hydrogen, tetahydropyranyl or

R'' is phenyl substituted with carboxyl, R$_2$ is —(CH$_2$)$_m$—CH$_3$, m is 3,4 or 5 or R$_1$ and R$_2$ are =CH—(CH$_2$)$_n$—CH$_3$ and n is 2,3 or 4.

Another preferred groups of compounds of formula I are those where the dotted line is a second bond, A is a simple bond, R is hydrogen or alkynyl or alkenyl of 2 to 3 carbon atoms, R$_1$ is OH and R$_2$ is —(CH$_2$)$_4$—CH$_3$.

Among the prefered compounds of formula I' are the lactone of (1RS, 2SR, 5RS, 3'SR)(1'E) 2-hydroxy-5-(3'-hydroxy-1'-octenyl) cyclopentane carboxylic acid, the lactone of (1RS, 2SR, 5RS, 3'SR)(1'E) 2-hydroxy-5-(3'-hydroxy-1'-decenyl) cyclopentane carboxylic acid and the lactone of (1RS, 2SR, 5RS, 3'SR)(1'E) 2-hydroxy-5-[3'-(2''-hydroxybenzoyloxy)-1'-octenyl]cyclopentane carboxylic acid.

The novel process of the invention for the preparation of a compound of formula I', particularly formula I, comprises reacting a compound of the formula

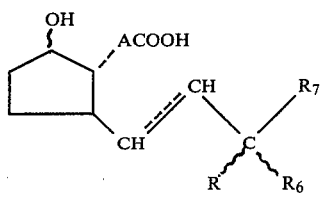

wherein A, R, $R_6$ and $R_7$ have the above definition with a reactant of formation of a functional derivative of an acid to obtain a compound of formula I', or a product of the formula

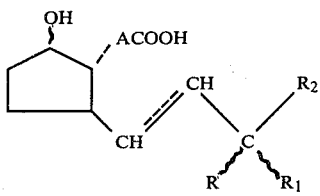

wherein A, R, $R_1$ and $R_2$ have the above definition with a reactant of formation of a functional derivative of an acid to obtain a compound of formula I, the functional derivative thus obtained in each case reacting then with a hydroxyl group to form the lactone ring to thus obtain a compound of formula I' or I.

In a preferred mode of the process of the invention, the reactant for the formation of the functional derivative of the acid to which one subjects the product of formulae IIa or II is tosyl chloride to form a functional derivative which is a mixed anhydride. The reaction is preferably effected in the presence of triethylamine but other bases such as alkali metal carbonates or other organic bases such as N-methyl morpholine, pyridine or other trialkylamines may be used. Equally useful is diazabicyclooctane.

One can also subject the compounds of formula II or IIa to the action of other reactants to form mixed anydrides such as isobutyl chloroformate or other alkyl chloroformates and the reaction is effected in the presence of a basic agent of the foregoing types. Other reactants equally useful are dialkylcarbodiimides or dicylcoalkylcarbodiimides such as dicyclohexylcarbodiimide. Also useful are the reactants for the formation of acid chlorides such as thionyl chloride in the presence of a basic agent of the above types.

The preferred mode of the process of the invention to form a compound of formula I or I' uses as reactant of formation of a functional derivative of an acid, tosyl chloride, alkyl chloroformates, dicycloalkylcarbodiimides, dialkylcarbodiimides or thionyl chloride and the basic agent is selected from the group consisting of alkali metal carbonates, triethylamine, N-methylmorpholine, pyridine and diazabicyclooctane.

Another object of the invention is a process for the preparation of a compound of the formula

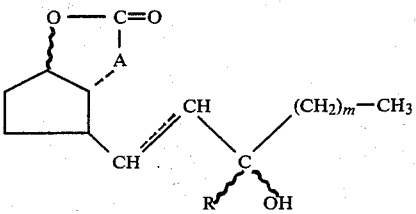

wherein the dotted line m, A and R have the above definition which corresponds to a compound of formula I wherein $R_1$ is OH and $R_2$ is $-(CH_2)_m-CH_3$, comprising reacting a compound of the formula

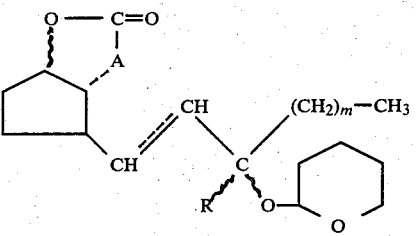

with an acid hydrolysis agent.

The compounds of formula IA used as the starting material may be prepared by reacting a compound of the formula

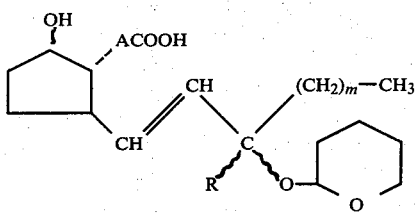

wherein A, R and m have the above definition, with a reactant for the formation of a functional derivative of an acid.

In a preferred mode of the process for the preparation of formula $I_B$, the hydrolysis is effected in the presence of acetic acid but other mineral or organic acids such as aqueous hydrochloric acid, sulfuric acid or trifluoroacetic acid may be used.

The process of the invention for the preparation of a compound of the formula

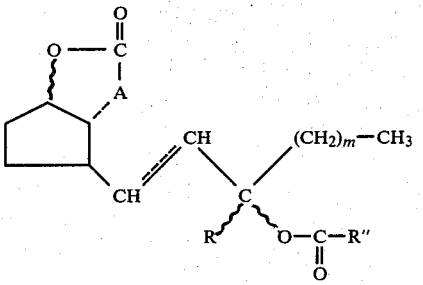

wherein A, R, R" and m have the above definition and corresponds to a compound of formula I wherein $R_1$ is OR', R' is

and $R_2$ is $-(CH_2)_m-CH_3$, comprises reacting an acid of the formula $R''-COOH$ or its acid chloride, acid anhydride or mixed anhydride with a compound of formula IB.

A preferred mode of the process uses the acid anhydride of the formula $(R''CO)_2O$ but equally useful is the acid chloride of the formula $R''COCl$ and the reaction is then effected in the presence of an acid acceptor such as an alkali metal carbonate or dicarbonate or an tertiary organic base such as triethylamine, pyridine or a picoline.

Another mode of the process of the invention for the preparation of a compound of the formula

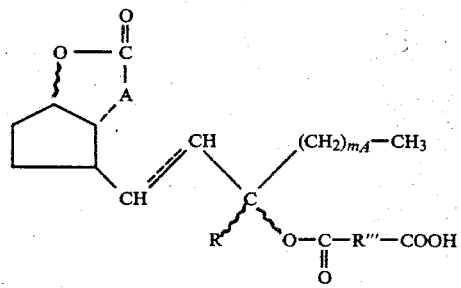

I'C wherein R, A and $m_A$ have the above definition and $R'''$ is alkylene of 1 to 3 carbon atoms corresponding to a compound of formula I' wherein $R_7$ is $-(CH_2)_{m_A}-CH_3$ and $R_6$ is

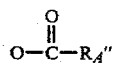

and $R_A''$ is alkyl of 1 to 3 carbon atoms substituted with carboxyl, comprising reacting a compound of the formula

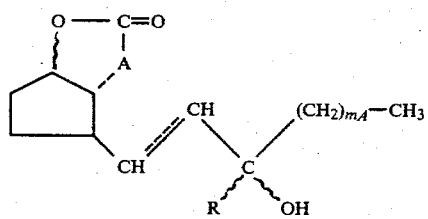

I'B wherein the dotted line, R, A and $m_A$ have the above definition corresponding to a compound of formula I' wherein $R_6$ is $-OH$ and $R_7$ is $-(CH_2)_{m_A}-CH_3$, with an acid anhydride of the formula $(R'''CO)_2-O$.

The said process is preferably effected in the presence of a tertiary organic base such as triethylamine, pyridine, dimethylaminopyridine, a picoline or mixtures thereof. The compounds of formula I'B may be prepared for example by the described methods beginning with products of formulae IIa or II corresponding, according to the value of $m_A$.

The process of the invention also includes the preparation of a compound of the formula

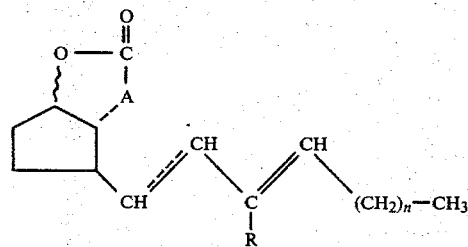

ID wherein A, R and n have the above definition and corresponding to a compound of formula I wherein $R_1$ and $R_2$ are $=CH-(CH_2)_n-CH_3$ comprising reacting a compound of formula IA or IB with a dehydration agent, preferably p-toluene sulfonic acid. Also useful are strong aqueous acids such as concentrated sulfuric acid or phosphoric acid or polyphosphoric acid.

The process for the preparation of a compound of the formula

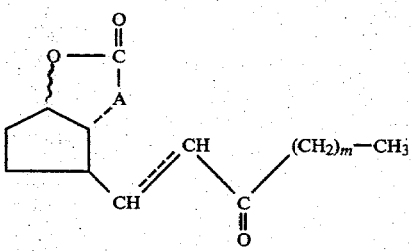

IE wherein A and m have the above definition and corresponding to a compound of formula I wherein R and $R_1$ are $=O$ and $R_2$ is $-(CH_2)_m-CH_3$ comprises reacting a compound of the formula

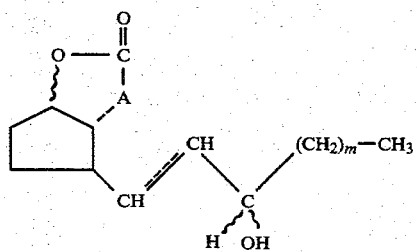

I''B with an oxidizing agent, preferably dichlorodicyanoquinone. Also useful are other oxidizing agents such as silver silicate. The products of formula I''B may be prepared from the products of formula II with the process of the invention.

The process for the preparation of a compound of the formula

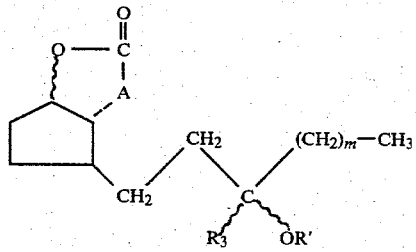

IF wherein A, R' and m have the above definitions and $R_3$ is hydrogen or alkyl corresponding to a compound of formula I wherein R is hydrogen or alkyl, $R_1$ is OR' and $R_2$ is —$(CH_2)_m$—$CH_3$ comprises reacting a compound of the formula

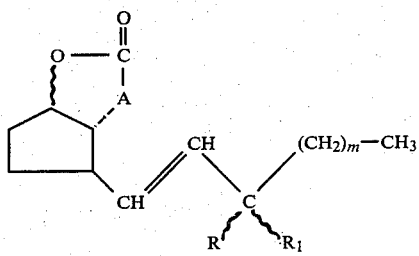

wherein A, m, R and $R_1$ have the above definition except R and $R_1$ are not keto with hydrogen in the presence of a catalyst. The preferred catalyst is palladized carbon but also useful are platinum, platinum salts and other supports such as barium sulfate. The compounds of formula I'F may be prepared by the process of the invention starting from the compounds of formula II.

The process for the preparation of a compound of the formula

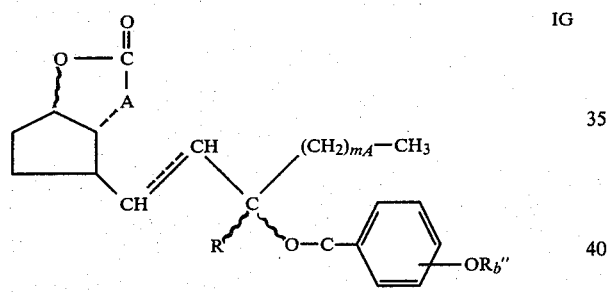

IG wherein A, R and $m_A$ have the above definition and $R_b''$ is hydrogen, acyl of an alkanoic acid of 2 to 4 carbon atoms or an easily hydrolyzable group corresponding to a compound of formula I' wherein $R_7$ is —$(CH_2)_{mA}$—$CH_3$ and $R_6$ is

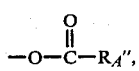

$R_A''$ is phenyl substituted with hydroxy or a hydroxy protected with an acyl group or an easily hydrolyzable group comprising reacting a compound of formula I'B with a functional derivative of an acid of the formula

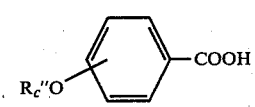

wherein $R_c''$ is acyl of an alkanoic acid of 2 to 4 carbon atoms or an easily hydrolyzable group to obtain a compound of the formula

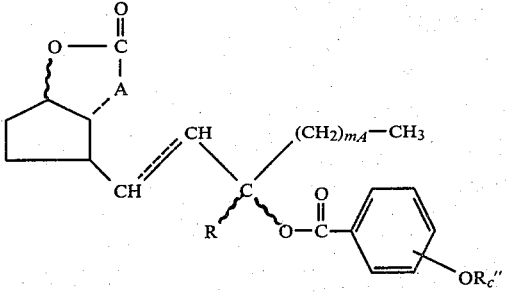

I'G which may be treated with an acid or base to form the corresponding compound of formula IG wherein $R_b''$ is hydrogen.

The preferred functional derivative of the acid is the acid halide, preferably the chloride but may be the bromide and the reaction is effected in the presence of an acceptor of hydrochloric acid or hydrobromic acd such as triethylamine or a picoline. Other functional derivatives of the acid are mixed anhydrides prepared, for example by reaction of the acid with oxalyl chloride or ethyl chloroformate or isobutyl chloroformate. Also useful are active acid esters, or the azide or amide of the acid.

When $R_c''$ is acyl of an alkanoic acid of 2 to 4 carbon atoms, the hydrolysis is preferably a basic hydrolysis effected with sodium carbonate but other bases such as sodium hydroxide or potassium hydroxide in methanol or ethanol may also be used. When $R_c''$ is an easily hydrolyzable group, the hydrolysis is an acid hydrolysis. If $R_c''$ is tetrahydropyranyl, the medium is preferaby oxalic acid but other acids such as acetic acid or trifluoroacetic acid may be used.

The process for the preparation of a compound of the formula

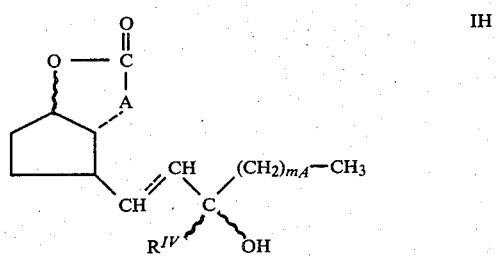

IH wherein A and $m_A$ have the above definition and $R^{IV}$ is alkenyl of 2 to 4 carbon atoms, each of the doubly-linked carbon comporting at least one hydrogen, corresponding to a compound of formula I' wherein R=$R^{IV}$, $R_6$ is —OH and $R_7$ is —$(CH_2)_{mA}$—$CH_3$ comprises reacting a compound of the formula

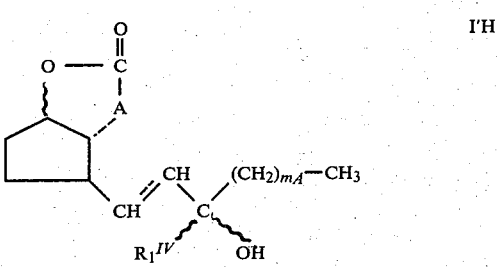

I'H wherein $R_1^{IV}$ is alkynyl of 2 to 4 carbon atoms with hydrogen in the presence of a catalyst.

The catalyst is preferably palladium on barium sulfate with a trace of quinoline. Also useful are palladium on calcium carbonate in the presence of lead acetate or palladium on carbon black in the presence of pyridine or Raney nickel. The products of formula I'H may be prepared by the preceding method starting from compounds of formula IIa or II corresponding, according to the value of $m_A$.

The wavy lines in the various formulae indicate the diverse possible configurations of the substituents about the carbon atoms to which they are attached. The constituents of the mixtures eventually formed of the different products may be separated by the usual physical methods such as chromatography. The products of formulae I' and I exist as racemic mixtures or optically active isomers which can be separated by the known methods.

The novel hypotensive compositions of the invention are comprised of a hypotensively effective amount of at least one compound of formula I or I' and an inert pharmaceutical carrier or excipient. The compositions may be in the form of tablets, dragees, gelules, granules, suppositories or injectable solutions or suspensions. Examples of suitable excipients are talc, arabic gum, starch, lactose, magnesium stearate, cacao butter and aqueous or non-aqueous vehicles.

The compositions of the invention are useful for the treatment of hypertension and circulatory troubles.

The novel method of the invention for relieving hypertension in warm-blooded animals, including humans, comprises administering to warm-blooded animals a hypotensively effective amount of at least one compound of formula I or I'. The compounds may be administered orally, rectally, locally, or parenterally. The usual daily dose is depending upon the compound and the method of administration. For example, the products of Examples 2 and 15 when injected by slow perfusion in humans may be used at a dose of 0.01 to 4 mg/kg.

The novel intermediate products of the invention for the preparation of compounds of formula I' have the formula

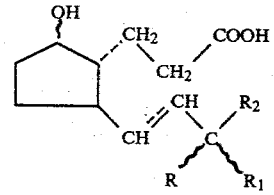

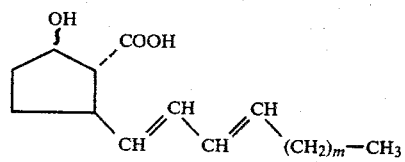

wherein R, $R_1$ and $R_2$ and the dotted line have the above definition, wherein m has the above definition and

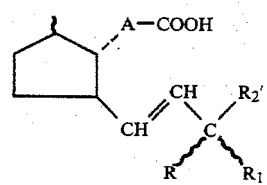

wherein the dotted line and A, R and $R_1$ have the above definitions and $R_2'$ is $-(CH_2)_6-CH_3$ or $R_1$ and $R_2'$ are $=CH-(CH_2)_5-CH_3$.

The products of formula II used as starting materials and wherein A is a simple bond and $R_1$ and $R_2$ are not $=CH-(CH_2)_m-CH_3$ and m is 4 may be prepared by the process of commonly assigned, copending U.S. patent application Ser. No. 717,048 filed Aug. 24, 1976, now U.S. Pat. No. 4,109,009 wherein a compound of the formula

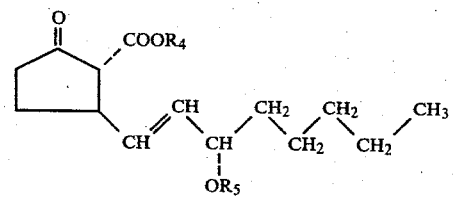

wherein $R_4$ is alkyl of 1 to 12 carbon atoms and $R_5$ is hydrogen or 2-tetrahydropyranyl is reacted with alkali metal hydride under mild conditions to obtain a compound of the formula

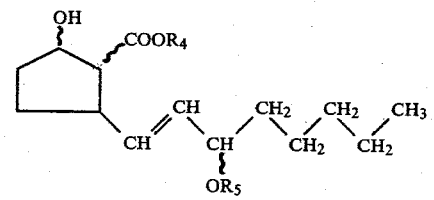

which may be further treated if desired either (a) with hydrogen in the presence of a catalyst to obtain a compound of the formula

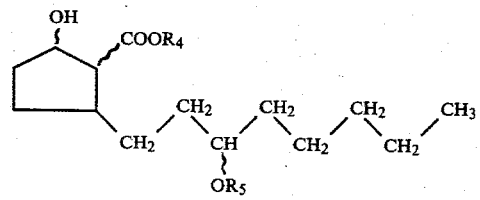

or (b) with an alkaline base and then an acid to obtain a compound of the formula

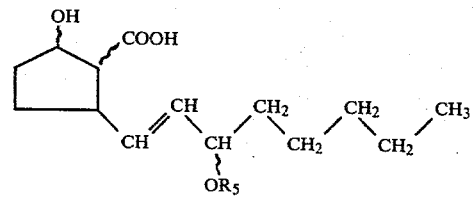

or (c) if R is hydrogen with an oxidizing agent to obtain a compound of the formula

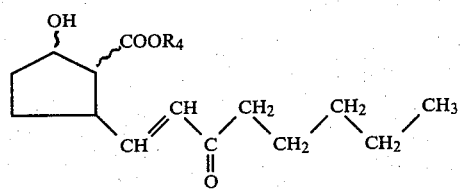  F and the latter may be treated with an organometallic compound of the formula

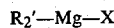

wherein $R_2'$ is branched or straight chain, saturated or nonsaturated alkyl of 1 to 4 carbon atoms and X is halogen to form a compound of the formula

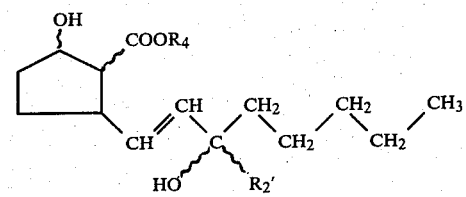  G

The compound of formula B, wherein $R_5$ is hydrogen may be reacted with diazomethane to obtain a compound of the formula

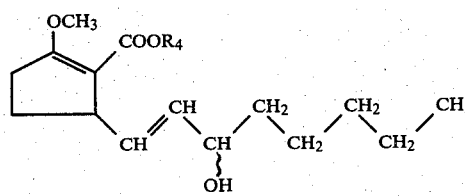  H which may be reacted with an oxidizing agent to form a compound of the formula

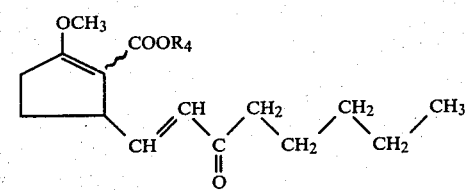  H' which is treated with an organometallic or organo metalloidic derivative of the formula $R_2'$—Mg—X to obtain a compound of the formula

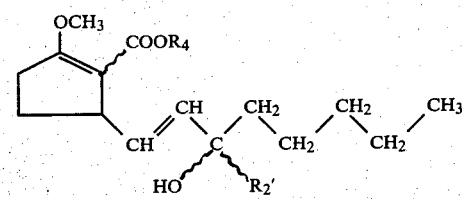  J which is treated with an acid to form a compound of the formula

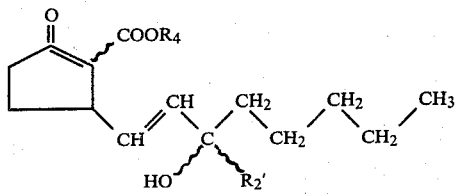  K which is then either treated with a reducing agent under mild conditions to form the product of formula G or with dihydro-2,3-pyran to obtain a compound of the formula

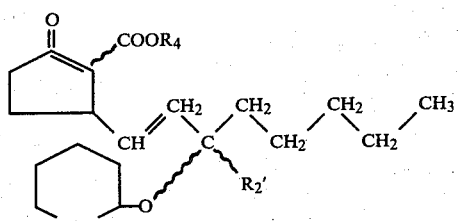  K' which is then reacted with a reducing agent under mild conditions to obtain a compound of the formula

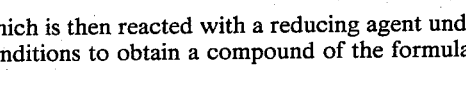

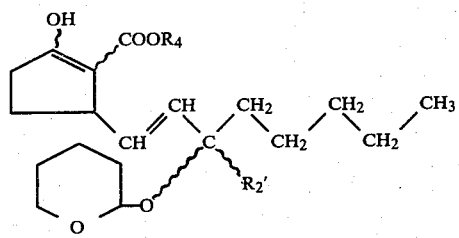  L and treating the compounds of formulae D,F,G or L with a base and then an acid to obtain the corresponding acids of formula II.

The compounds of formula II wherein $R_1$ and $R_2$ are =CH—$(CH_2)_3$—$CH_3$ and A is a simple bond may be prepared by reacting a compound of formula B wherein $R_5$ is 2-tetrahydropyranyl with 2,4-dinitrobenzene sulfinyl chloride.

The compounds of formula II wherein A is —$(CH_2)_2$—, m is 4 or $R_1$ and $R_2$ are =CH—$(CH_2)_n$—$CH_3$ and n is 3 may be prepared by subjecting a compound of the formula

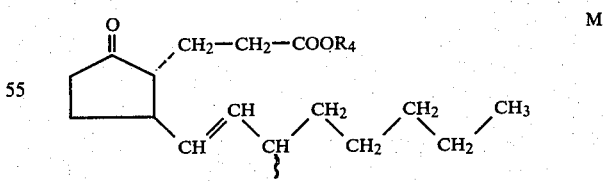  M to the same reaction as the compound of formula B. The compounds of formula M may be prepared by reacting a compound of formula B wherein $R_5$ is 2-tetrahydropyranyl with an alkyl acrylate followed by an isomerization and a decarboxylation.

The products of formula II wherein m is 3 or 5 or n is 2 or 4 may be prepared from a compound of the formula

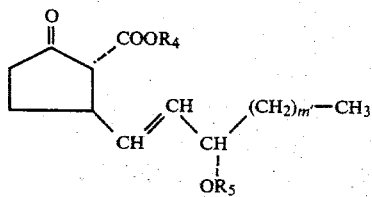

wherein m' is 3 or 5 and the method of preparation is identical to that to prepare the products of formula B. The compounds of formula II wherein A is —(CH$_2$)$_2$— are prepared from compounds of the formula

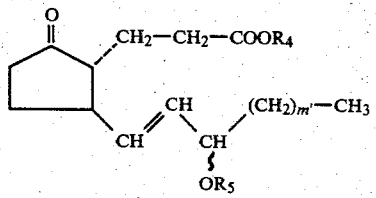

which are obtained by the process above starting with compounds of formula B'.

The products of the formula

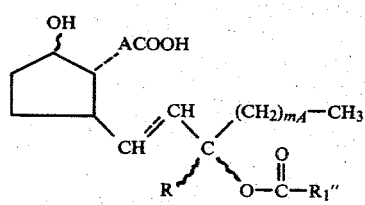

wherein R and m$_A$ have the above definition and R$_1''$ is alkyl of 1 to 3 carbon atoms substituted with a carboxyl or phenyl substituted with —OH or acyloxy of 2 to 4 carbon atoms or hydroxyl protected with an easily hydrolyzable group and A is a simple bond, may be prepared from a compound of the formula

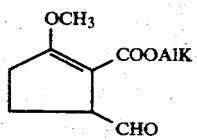

wherein AlK is alkyl of 1 to 4 carbon atoms by the process comprising reacting 2,3-epoxy-propanol with dihydropyran to obtain 1,2-epoxy-3α-tetrahydropyranyloxypropane, reacting the latter with an alkyl acetylacetate in the presence of a strong base such as sodium hydride-butyllithium to obtain a compound of the formula

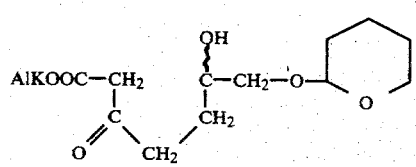

reacting the latter with an oxidation agent such as a complex of pyridine-chromic acid to obtain a compound of the formula

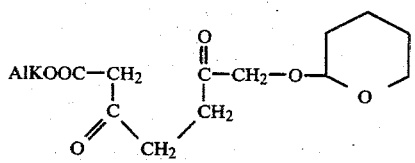

reacting the latter with a base such as potassium bicarbonate to obtain a compound of the formula

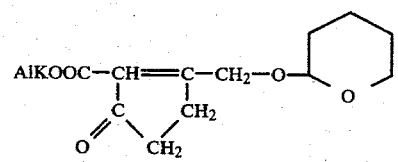

reacting the latter with hydrogen in the presence of a catalyst such as palladized carbon to obtain a compound of the formula

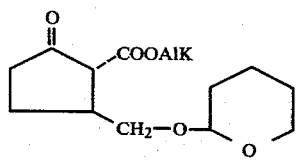

reacting the latter with an acid to obtain a compound of the formula

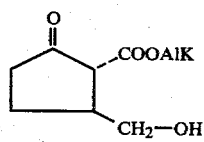

reacting the latter with diazomethane to obtain a compound of the formula

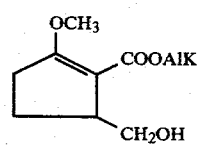

and reacting the latter with an oxidizing agent such as pyridine-chromic acid complex to obtain the corresponding compound of formula A'.

To prepare the compounds of formula II$_a'$, the compound of formula A' is reacted with dimethyl (2-oxononyl) phosphonate in the presence of a strong base such as sodium hydride to obtain a compound of the formula

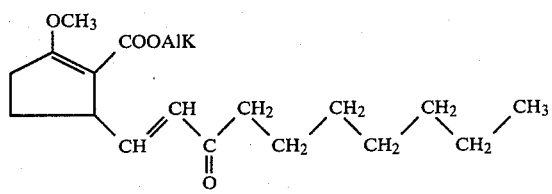

reacting the latter with a reducing agent such as zinc borohydride to obtain a compound of the formula

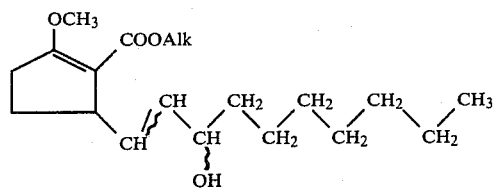

in the form of a mixture of the two constituents which can be separated into its two isomers and the hydroxyl group is protected with tetrahydropyranyl and the latter is treated with an acid such as hydrochloric acid, then with a reducing agent such as L selectride and finally with a base such as sodium hydroxide followed by acid treatment such as monosodium phosphate to obtain a compound of the formula

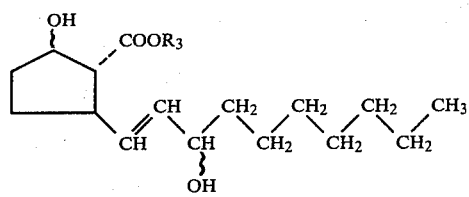

B₁ wherein $R_3$ is hydrogen or alkyl of 1 to 4 carbon atoms. To obtain a compound of the formula

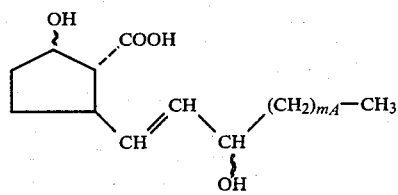

B₂ wherein $m_A$ has the above definition, analogous procedures are applied as to the products of formulae B₁ and E.

The compounds of formula II$_a$' wherein A is a simple bond may be prepared by reacting a compound of formula B₂ either with an acid anhydride of the formula

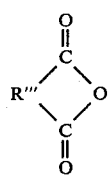

or an acid or functional derivative thereof of the formula

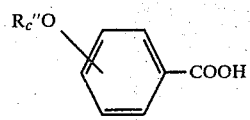

followed by hydrolysis identical to conditions indicated for the synthesis of compounds of formula I'C and IG from the products of formula I'B. The compounds of formula II$_a$' wherein A is —(CH₂)₂— can be prepared with the same reactants starting with a compound of the formula

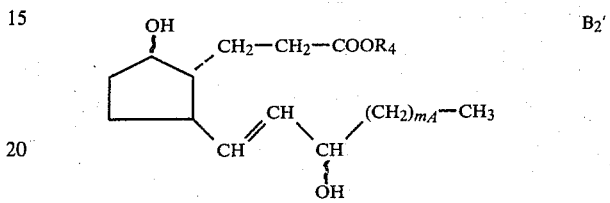

B₂'

Finally, the compounds of formula II$_A$ not having a double bond therein may be obtained by hydrogenation of the corresponding compounds with a double bond.

The compounds of formula IIH can be prepared in the same fashion indicated above for the corresponding compounds of formula II but using as the starting material a compound of the formula

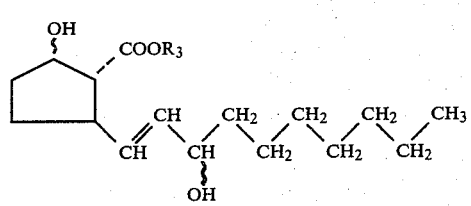

B or a compound of the formula

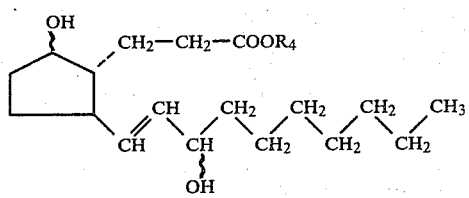

The preparation processes can be summarized as follows: either treating the compounds of B₁ or B₂' with hydrogen in the presence of a catalyst to obtain the corresponding saturated compounds or treating the same compounds with an oxidation agent to selectively oxidize the allylic alcohol to obtain compounds wherein R and R₁ form a keto group then treating the resulting products with an organometallic derivative to obtain a compound wherein R is alkyl or reacting a compound of formula B₁ or B₂' with the allylic hydroxyl protected with tetrahydropyranyl with 2,4-dinitrobenzene sulfinyl chloride to obtain compounds wherein R₁ and R₂' are =CH—(CH₂)₅—CH₃. The corresponding acids can be prepared by saponification of the esters by the usual methods.

In the following examples there are described several preferred embodiments to illustrate the invention. However, it should be understood that the invention is not intended to be limited to the specific embodiments.

EXAMPLE 1 lactone of (1RS, 2SR, 5RS, 3'SR)(1'E) 2-hydroxy-5-(3'α-tetrahydropyranyloxy-1'-octenyl)-cyclopentane carboxylic acid STEP A: ethyl (1RS, 2SR, 5RS, 3'SR)(1'E) 2-hydroxy-5-(3'α-tetrahydropyranyloxy-1'-octenyl)-cyclopentane carboxylate A mixture of 14 g of ethyl 3-(3'α-tetrahydropyranyloxytrans-1'-octenyl)-cyclopentanone-2-carboxylate, 200 ml of isopropanol, 20 ml of water and 5.6 g of sodium borohydride was stirred for 2 hours and then acetone was slowly added to the mixture. The mixture was then added to an aqueous solution saturated with monosodium phosphate and the mixture was filtered. The filtrate was evaporated to dryness and the residue was taken up in ethyl acetate. The solution was washed with water, dried and evaporated to dryness. The residue was chromatographed over silica gel and was eluted with an 8-2 cyclohexane-ethyl acetate mixture containing 0.1% triethylamine to obtain 3.4 g of ethyl (1RS, 2SR, 5RS, 3'SR) (1'E) 2-hydroxy-5-(3'α-tetrahydropyranyloxy-1'-octenyl)-cyclopentane-carboxylate (α-OH isomer).

STEP B: (1RS, 2SR, 5RS, 3'SR)(1'E) 2-hydroxy-5-(3'α-tetrahydropyranyloxy-1'-octenyl)-cyclopentane-carboxylic acid A mixture of 3.1 g of the product of Step A, 50 ml of methanol and 8.15 ml of 2 N sodium hydroxide was stirred for 3 hours and the solvents were evaporated at 35°–40° C. The residue was taken up in water and the solution was washed with ether and then an aqueous solution saturated with sodium chloride. The solution was acidified with hydrochloric acid and was extracted with ether. The ether extracts were washed with water, dried and evaporated to dryness to obtain 2.6 g of (1RS, 2SR, 5RS, 3'SR)(1'E) 2-hydroxy-5-(3'α-tetahydropyranyloxy-1'-octenyl)-cyclopentane-carboxylic acid.

STEP C: lactone of (1RS, 2SR, 5RS, 3'SR)(1'E) 2-hydroxy-5-(3'α-tetrahydropyranyloxy-1'-octenyl)-cyclopentane carboxylic acid A mixture of 600 mg of the product of Step B, 12 ml of anhydrous chloroform, 1 ml of triethylamine and 402 mg of tosyl chloride was stirred for 4 hours at 20° C. and was poured into a saturated solution of monosodium phosphate. The mixture was decanted and the aqueous phase was extracted with methylene chloride. The organic extracts were evaporated to dryness under reduced pressure to obtain 700 mg of product which was chromatographed over silica gel. Elution with a 3-1 cyclohexane-ethyl acetate mixture containing 0.1% of triethylamine yielded 336 mg of the β-lactone of (1RS, 2SR, 5RS, 3'SR)(1'E) 2-hydroxy-5-(3'α-tetrahydropyranyloxy-1'-octenyl)-cyclopentane-carboxylic acid.

EXAMPLE 2 lactone of (1RS, 2SR, 5RS, 3'SR)(1'E) 2-hydroxy-5-(3'α-hydroxy-1'-octenyl)-cyclopentane carboxylic acid A solution of 336 mg of the product of Example 1 in 10 volumes of acetic acid containing 20% of water in the presence of 5 mg of sodium iodide stood for 16 hours at 20° C. and was then poured into water. The mixture was extracted with methylene chloride and the organic extracts were washed with sodium bisulfite and then dried to obtain 280 mg of product. The latter was chromatographed over silica gel and was eluted with a 3-1 cyclohexane-ethyl acetate mixture to obtain 160 mg of the lactone of (1RS, 2SR, 5RS, 3'SR)(1'E) 2-hydroxy-5-(3'α-hydroxy-1'-octenyl)-cyclopentane carboxylic acid.

EXAMPLE 3 lactone of (1RS, 2SR, 5RS, 3'SR)(1'E) 2-hydroxy-5-(3'α-hemiphthaloyloxy-1'-octenyl)-cyclopentane carboxylic acid A mixture of 160 mg of the product of Example 2, 1.6 ml of pyridine and 200 mg of phthalic anhydride stood at room temperature for 9 days and was then poured into an iced N hydrochloric acid. The mixture was extracted with ether and the ether extracts were washed with 10% sodium bicarbonate solution, dried and evaporated to dryness under reduced pressure. The aqueous alkaline phase was acidified with N hydrochloric acid, was extracted with ether and evaporated to dryness. The acid fraction was chromatographed over silica gel and was eluted with a 1-1cyclohexane-ethyl acetate mixture to obtain 172 mg of (1RS, 2SR, 5RS, 3'SR)(1'E 2-hydroxy-5-(3'α-hemiphthaloyloxy-1'-octenyl)-cyclopentane carboxylic acid in the form of a colorless resin which crystalizes. IR Spectrum: 1828 and 1811 cm$^{-1}$ (carbonyl of β-lactone), 1725 and 1708 cm$^{-1}$ (carbonyl of ester and carboxyl) and 1603, 1583 and 1491 cm$^{-1}$ (aromatic ring).

EXAMPLE 4 lactone of (1RS, 2SR, 5RS, 3'SR)(1'E) 2-hydroxy-5-(3'-hydroxy-3'-ethynyl-1'-octenyl)-cyclopentane carboxylic acid A mixture of 530 mg of (1RS, 2SR, 5RS, 3'SR)(1'-E) 2,3'-dihydroxy-5-(3'-ethynyl-1'-octenyl)-cyclopentane carboxylic acid, 5.3 ml of chloroform, 0.78 ml of triethylamine and 430 mg of tosyl chloride were stirred at 5° C. for 30 minutes and after the temperature returned to 20° C., the mixture stood for an hour and was then poured into aqueous monosodium phosphate solution. The mixture was washed with water and was extracted with methylene chloride. The extracts were evaporated to dryness and the residue was chromatographed over silica gel. Elution with a 4-1 benzene-ethyl acetate mixture yielded 106 mg of the lactone of (1RS, 2SR, 5RS, 3'SR)(1'E) 2-hydroxy-5-(3'α-hydroxy-3'-ethynyl-1'-octenyl)-cyclopentane carboxylic acid with an RF=0.4.

EXAMPLE 5

Lactone of (1RS, 2SR, 5RS, 3'RS)(1'E) 2-hydroxy-5-(3'-hydroxy-3'-ethynyl-1'-octenyl)-cyclopentane carboxylic acid STEP A: ethyl (1RS, 2SR, 5RS, 3'SR)(1'E) 2-hydroxy-5-(3'-hydroxy-1'-octenyl)-cyclopentane carboxylate A mixture of 572 mg of ethyl 3-(3'α-hydroxy trans-1'-octenyl)-cyclopentanone-2-carboxylate, 23 ml of ethanol, 2.3 ml of water and 85 mg of sodium borohydride was stirred for two hours at 5° C. and a few drops of acetone were then added thereto. The mixture was poured into a saturated monosodium phosphate solution and was then filtered. The filtrate was evaporated to dryness and the residue was taken up in ethyl acetate. The solution was washed with water, dried and evaporated to dryness to obtain a mixture of 2α-OH and 2β-OH isomers. The latter was chromatographed over silica gel and was eluted with ethylene chloride containing 2% of methanol to obtain 203 mg of ethyl (1RS, 2SR, 5RS, 3'SR((1'E) 2-hydroxy-5-(3'-hydroxy-1'-octenyl)-cyclopentane carboxylate STEP B: ethyl (1RS, 2SR, 5RS)(1'E) 2-hydroxy-5-3'-oxo-1'-octenyl)-cyclopentane carboxylate 1.6 g of dichlorodicyanoquinone was added to a mixture of 1 g of the product of Step A in 20 ml of dioxane and the mixture was stirred 20 hours at room temperature and was then vacuum filtered. The filter was rinsed and the filtrate was washed with iced N/10 sodium hydroxide until the pH was 9. The mixture was filtered and the recovered product was washed with water and dried to obtain 987 mg of raw product. The product was chromatographed over silica gel and was eluted with a 1-1 cyclohexane-ethyl acetate mixture to obtain 930 mg of ethyl (1RS, 2SR, 5RS,)(1'E) 2-hydroxy-5-(3'-oxo-1'-octenyl)-cyclopentane carboxylate.

STEP C: ethyl (1RS, 2SR, 5RS, 3'SR and RS)(1'E) 2-hydroxy-5-(3'-hydroxy-3'-ethynyl-1'-octenyl)-cyclopentane carboxylate A mixture of 2.1 g of the product of Step B and 2.1 ml of tetrahydrofuran was heated to 38° C. and 45 ml of a solution of N ethynyl magnesium bromide in tetrahydrofuran heated to 40° C. was rapidly added thereto. The mixture was stirred at 38° C. for 30 minutes and was then poured into an ice solution of ammonium chloride in water. The mixture was extracted with methylene chloride and the organic extracts were washed with water, dried and filtered. The filtrate was evaporated to dryness and the residue was chromatographed over silica gel. Elution with an 85-15 methylene chloride-ethyl acetate mixture yielded 1.67 g of ethyl (1RS, 2SR, 5RS, 3'SR and RS)(1'E) 2-hydroxy-5-(3'-hydroxy-3'-ethynyl-1'-octenyl)-cyclopentane carboxylate.

STEP D: (1RS, 2SR, 5RS, 3'SR)(1'E) 2-hydroxy-5-(3'-hydroxy-3'-ethynyl-1'-octenyl)-cyclopentane carboxylic acid and (1RS, 2SR, 5RS, 3'RS)(1'E) 2-hydroxy-5-(3'-hydroxy-3'-ethynyl-1'-octenyl)-cyclopentane carboxylic acid A mixture of 1.67 g·of the product of Step C, 17 ml of ethanol and 8.5 ml of N sodium hydroxide was stirred under nitrogen for 2 hours at 20° C. and was then poured into water. The mixture was extracted with ether and the ether extracts were washed with 0.5 N sodium hydroxide solution, then with water, diluted and filtered to remove 0.37 g of impurities. The combined aqueous phases were acidified with monosodium phosphate and were extracted with ether. The ether phase was washed with water, dried and evaporated to dryness to obtain 1.33 g of product. The latter was chromatographed under pressure with isopropyl ether containing 4% of acetic acid to obtain 530 mg of (1RS, 2SR, 5RS, 3'SR)(1'E) 2-hydroxy-5-(3'-hydroxy-3'-ethynyl-1'-octenyl)-cyclopentane carboxylic acid with an Rf=0.15 and 720 mg of (1RS,2SR, 5RS, 3'RS) (1'E) 2-hydroxy-5-(3'-hydroxy-3'-ethynyl-1'-octenyl)-cyclopentane carboxylic acid with an Rf=0.10.

STEP E: lactone of (1RS, 2SR, 5RS, 3'RS)(1'E) 2-hydroxy-5-(3'-hydroxy-3'-ethynyl-1'-octenyl)-cyclopentane carboxylic acid A mixture of 720 mg of the 3'RS isomer of Step D, 7.2 ml of chloroform, 1.44 ml of triethylamine and 586 mg of tolsyl chloride was stirred at 20° C. under nitrogen and was then poured into an aqueous solution of monosodium phosphate. The mixture was washed with water and was extracted with methylene chloride. The organic phase was dried and evaporated to dryness to obtain about 1 g of product. The latter was chromatographed over silica gel and was eluted with a 4-1 benzene-ethyl acetate mixture to obtain 128 mg of the lactone of (1RS, 2SR, 5RS, 3'RS)( 1'E) 2-hydroxy-5-(3'-hydroxy-3'-ethynyl-1'-octenyl)-cyclopentane carboxylic acid with an RF=0.4.

EXAMPLE 6 lactone of (1RS, 2SR, 5RS)(1'E, 3'E) 2-hydroxy-5-(1',3'-octadienyl)-cyclopentane carboxylic acid A mixture of 150 mg of the product of Example 2 in 3 ml of benzene was admixed with 15 mg of p-toluene sulfonic acid and the mixture was heated at 40° C. for 3 hours. The mixture was neutralized with 150 mg of sodium carbonate and was filtered. The filtrate was evaporated to dryness to obtain 139 mg of an oil which was chromatographed over silica gel. Elution with a 95-5 cyclohexane-ethyl acetate mixture yielded 36 mg of the pure lactone of (1RS, 2SR, 5RS)(1'E,3'E) 2-hydroxy-5-(1',3'-octadienyl)-cyclopentane carboxylic acid with an Rf=0.25 (90-10 cyclohexane-ethyl acetate).

IR Spectrum (chloroform):

1830 cm$^{-1}$ (carbonyl),
shoulder at 1816 cm$^{-1}$, 993 cm$^{-1}$ (〜〜〜)

U.V. Spectrum (ethanol):

| inflexion = 227 nm | $E_{1cm}^{1\%}$ = 1310 cm$^{-1}$ | |
| max. = 232 nm | $E_{1cm}^{1\%}$ = 1410 cm$^{-1}$ | ε = 31,000 |
| inflexion = 239 nm | $E_{1cm}^{1\%}$ = 1044 cm$^{-1}$ | |

EXAMPLE 7 lactone of (1RS, 2SR, 5RS, 3'SR)(1'E) 2-hydroxy-5-(3'-hydroxy-1'-octenyl)-cyclopentane propionic acid STEP A: ethyl (5RS, 3'SR)(1'E) 1-ethyl carboxylate-2-oxo-5-(3'α-tetrahydropyranyloxy-1'-octenyl)-cyclopentane propionate 0.23 ml of a solution of 0.22 N sodium ethylate in ethanol was added under nitrogen to a mixture of 1.113 g of ethyl 3-(3'α-tetrahydropyranyloxy trans-1'-octenyl)-cyclopentanone-2-carboxylate and 3 ml of anhydrous ethanol and 303 mg of ethyl acrylate were added thereto. The mixture stood for 2 hours at 25° C. and was then refluxed for an hour. After cooling to 0° C., the mixture was poured in an iced monosodium phosphate solution and the mixture was extracted with ether. The ether extracts were washed with water, dried and evaporated to dryness under reduced pressure. The residue was chromatographed over silica gel and was eluted with an 8-2 cyclohexane-ethyl acetate mixture containing 0.1% triethylamine to obtain 1.13 g of ethyl (5RS, 3′SR)(1′E) 1-ethylcarboxylate-2-oxo-5-(3′α-tetrahydropyranyloxy-1′-octenyl)-cyclopentane propionate.

STEP B: ethyl (1RS, 5RS, 3′SR)(1′E) 2-oxo-3-carbethoxy-5-(3′α-tetrahydropyranyloxy-1′-octenyl)-cyclopentane propionate.

A mixture of 2.1 ml of a solution of 1.02 N sodium ethylate in ethanol and 0.93 g of the product of Step A was refluxed for 4 hours and 10 ml of toluene were added thereto. The ethanol was distilled and after cooling to −20° C., the mixture was added to an iced monosodium phosphate solution. The mixture was extracted with ether and the ether phase was washed with water and dried to obtain 940 mg of raw product. The latter was chromatographed over silica gel and was eluted with a 6-4 cyclohexane-ethyl acetate mixture to obtain 680 mg of ethyl (1RS, 5RS, 3′SR)(1′E) 2-oxo-3-carbethoxy-5-(3′α-tetrahydropyranyloxy-1′-octenyl)-cyclopentane propionate.

STEP C: methyl (1RS, 5RS, 3′SR)(1′E) 2-oxo-5-(3′α-tetrahydropyranyloxy-1′-octenyl)-cyclopentane propionate 9.6 ml of N sodium hydroxide solution were added to 1.5 g of the product of Step B in 20 ml of methanol and after standing at room temperature, the mixture was heated to 40° C. for 12 hours. The mixture was evaporated to dryness and the residue was taken up in a water-ethyl acetate mixture. The mixture was iced, acidified and extracted with ethyl acetate and the extracts were washed with water and evaporated to dryness to obtain 1.225 g of product. The latter was dissolved in 20 ml of benzene and the solution was refluxed for 1 hour to obtain 1.2 g of product. The latter was taken up in methylene chloride containing a drop of triethylamine. The product was reacted with diazomethane to obtain an oil which was chromatographed over silica gel. Elution with a 1-1 ethyl acetate-cyclohexane mixture yielded 852 mg of methyl (1RS, 5RS, 3′SR)(1′E) 2-oxo-5-(3′α-tetrahydropyranyloxy-1′-octenyl)-cyclopentane propionate.

STEP D: methyl (1RS, 2SR, 5RS, 3′SR)(1′E) 2-hydroxy-5-(3′α-tetrahydropyranyloxy-1′-octenyl)-cyclopentane propionate and methyl (1RS, 2RS, 5RS, 3′SR)(1′E) 2-hydroxy-5-(3′α-tetrahydropyranyloxy-1′-octenyl)-cyclopentane propionate 220 mg of sodium borohydride were added at 0° C. over 1 hour under nitrogen to a mixture of 2.165 g of the product of Step C and 21 ml of methanol and after stirring for 1 hour, the mixture was admixed with 30 ml of water and 3 g of monosodium phosphate. The mixture was extracted with methylene chloride and the extracts were washed with water and dried to obtain 2.014 g of product of the 2RS and 2SR isomers. The latter was chromatographed over silica gel and was eluted with a 50-50 mixture of ether and essence G (boiling between 35° and 70° C.) to obtain 329 mg of methyl (1RS, 2SR, 5RS, 3′SR) (1′E) 2-hydroxy-5-(3′α-tetrahydropyranyloxy-1′-octenyl)-cyclopentane propionate and 1.143 g of methyl (1RS, 2RS, 5RS, 3′SR)(1′E) 2-hydroxy-5-(3′α-tetrahydropyranyloxy-1′-octenyl)-cyclopentane propionate.

STEP E: methyl (1RS, 2SR, 5RS, 3′SR)(1′E) 2-hydroxy-5-(3′-hydroxy-1′-octenyl)-cyclopentane propionate A mixture of 458 g of the 2SR isomer of STEP D, 4.6 ml of methanol, 0.46 ml of water and 46 mg of oxalic acid was heated at 40° C. for 4 hours and methyl (1RS, 2SR, 5RS, 3′SR) (1′E) 2-hydroxy-5-(3′-hydroxy-1′-octenyl)-cyclopentane propionate in solution was obtained.

STEP F: (1RS, 2SR, 5RS, 3′SR)(1′E) 2-hydroxy-5-(3′-hydroxy-1′-octenyl)-cyclopentane propionic acid 3 ml of N sodium hydroxide solution were added at 40° C. under nitrogen to the solution of Step E and the mixture was heated at 40° C. for 2 hours and was then poured into an aqueous solution of monosodium phosphate. The mixture was extracted with ethyl acetate and the organic extracts were washed with water, dried, filtered and evaporated to dryness to obtain 390 mg of raw (1RS, 2SR, 5RS, 3′SR)(1′E) 2-hydroxy-5-(3′-hydroxy-1′-octenyl)-cyclopentane propionic acid.

STEP G: (1RS, 2RS, 5RS, 3′SR)(1′E) 2-hydroxy-5-(3′-hydroxy-1′-octenyl)-cyclopentane propionic acid A mixture of 479 mg of the 2RS isomer of Step D, 5 ml of methanol, 0.5 ml of water and 50 mg of oxalic acid was stirred at 40° C. for 3 hours and then 3 ml of N sodium hydroxide were added thereto. The mixture was stirred at 40° C. for another 3 hours and was then acidified with monosodium phosphate. The mixture was extracted with ethyl acetate and the organic extracts were washed with water and evaporated to dryness to obtain 405 mg of (1RS, 2RS, 5RS, 3′SR)(1′E) 2-hydroxy-5-(3′-hydroxy-1′-octenyl)-cyclopentane propionic acid.

STEP H: lactone of (1RS, 2SR, 5RS, 3′SR)(1′E) 2-hydroxy-5-(3′-hydroxy-1′-octenyl)-cyclopentane propionic acid A mixture of 390 mg of (1RS, 2SR, 5RS, 3′SR)(1′E) 2-hydroxy-5-(3′-hydroxy-1′-octenyl)-cyclopentane propionic acid, 3 ml of anhydrous nitromethane, 0.3 ml of pyridine and 300 mg of dicyclohexylcarbodiimide was stirred at 20° C. for 16 hours and was then vacuum filtered. The filtrate was washed with ether, dried and the organic phase was poured into water. The mixture was decanted and the aqueous phase was extracted with ether. The ether extracts were washed with water and were evaporated to dryness. The residue was chromatographed over silica gel and was eluted with a 1-1 cyclohexane-ethyl acetate mixture to obtain 173 mg of the homogenous lactone of (1RS, 2SR, 5RS, 3′SR)(1′E) 2-hydroxy-5-(3′-hydroxy-1′-octenyl)-cyclopentane propionic acid.

EXAMPLE 8 lactone of (1RS, 2RS, 5RS, 3′SR)(1′E) 2-hydroxy-5-(3′-hydroxy-1′-octenyl)-cyclopentane propionic acid A mixture of 405 mg of (1RS, 2RS, 5RS, 3′SR)(1′E) 2-hydroxy-5-(3′-hydroxy-1′-octenyl)-cyclopentane propionic acid, 3 ml of nitromethane, 0.3 ml of pyridine and 300 mg of dicyclohexylcarbodiimide were reacted as in Example 7 to obtain 188 mg of the pure lactone of (1RS, 2RS, 5RS, 3'SR)(1'E) 2-hydroxy-5-(3'-hydroxy-1'-octenyl)-cyclopentane propionic acid.

EXAMPLE 9 lactone of (1RS, 2SR, 5RS)(1'E) 2-hydroxy-(5-(3'-oxo-1'-octenyl) cyclopentane carboxylic acid 900 mg of chromic oxide were slowly added at 20° C. with cooling to a mixture of 15 ml of dry methylene chloride and 1.5 ml of pyridine under a nitrogen atmosphere and after stirring for 15 minutes, a solution of 358 mg of lactone of (1RS, 2SR, 5RS, 3'SR)(1'E) 2-hydroxy-5-(3'α-hydroxy-1'-octenyl) cyclopentane carboxylic acid in 15 ml of methylene chloride was rapidly added thereto. The mixture was stirred at 20° C. for 2 hours and then 4 g of celite and 15 ml of methylene chloride were added thereto. The mixture was filtered and the filtrate was concentrated under reduced pressure. Pyridine was removed with a nitrogen stream to obtain 375 mg of a brown oil. The latter was chromatographed over silica gel and was eluted with a 6-4 cyclohexane-ethyl acetate mixture to obtain 329 mg of the lactone of (1RS, 2SR, 5RS)(1'E) 2-hydroxy-5-(3'-oxo-1'-octenyl)-cyclopentane carboxylic acid with an Rf=0.45.

IR Spectrum:

1826 cm$^{-1}$ (β-lactone carbonyl) and 1696, 1674 and 1630 cm$^{-1}$ (  ).

EXAMPLE 10 lactone of (1RS, 2SR, 5RS, 3'SR) 2-hydroxy-5-(3'-hydroxy octanyl)-cyclopentane carboxylic acid A mixture of 105 mg of the lactone of (1RS, 2SR, 5RS, 3'SR)(1'E) 2-hydroxy-5-(3'α-hydroxy-1'-octenyl)-cyclopentane carboxylic acid in 10 ml of ethyl acetone and 20 mg of 5% palladized carbon were placed in a hydrogenation apparatus and hydrogen was added for 7 hours during which 10.4 ml of hydrogen were absorbed. The mixture was filtered to remove the catalyst and the filtrate was evaporated to dryness under reduced pressure. The oil residue was chromatographed over silica gel and was eluted with a 1-1 cyclohexane-ethyl acetate mixture to obtain 97 mg of the lactone of (1RS, 2SR, 5RS, 3'SR) 2-hydroxy-5-(3'-hydroxy octanyl)-cyclopentane carboxylic acid with an Rf=0.35.

IR Spectrum: 1800 cm$^{-1}$ (carbonyl), absence of C=C trans and 3600 cm$^{-1}$ (OH).

EXAMPLE 11 lactone of (1RS, 2SR, 5RS, 3'RS)(1'E) 2-hydroxy-5-(3'-hydroxy-3'-ethenyl-1'-octenyl)-cyclopentane carboxylic acid A mixture of 45 mg of barium sulfate containing 4.75% by weight of palladium and 5 ml of ethyl acetate was saturated with hydrogen at atmospheric pressure and 150 mg of the lactone of (1RS, 2SR, 5RS, 3'SR)(1'E) 2-hydroxy-5-(3'-hydroxy-3'-ethynyl-1'-octenyl)-cyclopentane carboxylic acid, 10 mg of quinoline and 1 ml of ethyl acetate were added thereto. The mixture was hydrogenated at 21° C. for about 30 minutes until 14.3 ml of hydrogen were absorbed and was then filtered to remove the catalyst. The filtrate was washed with 0.1 N hydrochloric acid and then with aqueous sodium chloride solution, was dried and evaporated to dryness to obtain 153 mg of raw product. The latter was chromatographed over silica gel and was eluted with a 4-1 benzene-ethyl acetate mixture and was then subjected to plate chromatography with the same eluant to obtain 110 mg of the lactone of (1RS, 2SR, 5RS, 3'RS)(1'E) 2-hydroxy-5-(3'-hydroxy-3'-ethenyl-1'-octenyl) cyclopentane carboxylic acid with an RF=0.41. The IR spectrum showed the absence of —C≡CH and the presence of β-lactone, ethenyl and hydroxy.

RMN Spectrum (CDCl$_3$ 60 MHz): (a) 0.88 ppm; (b) 1.51 ppm; (c) 3.1 ppm (triplet J=5 Hz); (d) doublet 3.8 ppm J=4 Hz; (e) 5.16 to 6.2 ppm; (f) 5 ppm (triplet J=3 Hz).

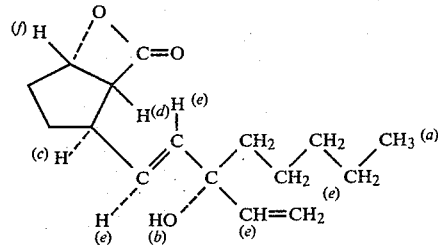

EXAMPLE 12 lactone of (1RS, 2SR, 5RS, 3'SR)(1'E) 2-hydroxy-5-(3'-hydroxy-3'-ethenyl-1'-octenyl)-cyclopentane carboxylic acid Using the procedure of Example 11, 150 mg of the lactone of (1RS, 2SR, 5RS, 3'RS)(1'E) 2-hydroxy-5-(3'-hydroxy-3'-ethynyl-1'-octenyl)-cyclopentane carboxylic acid were reacted to obtain 127 mg of pure lactone of (1RS, 2SR, 5RS, 3'SR)(1'E) 2-hydroxy-5-(3'-hydroxy-3'-ethenyl-1'-octenyl)-cyclopentane carboxylic acid. The IR spectrum showed the absence of C≡C and the presence of β-lactone, ethenyl and OH.

RMN Spectrum (CDCl$_3$ 60 MHz): (a) 0.88 ppm; (b) 1.51 ppm; (c) 3.1 ppm; (d) doublet 3.8 ppm J=4 Hz; (e) 5.16 to 5.61 ppm; (f) 5.16 to 6.2 ppm and; (g) 5 ppm (triplet).

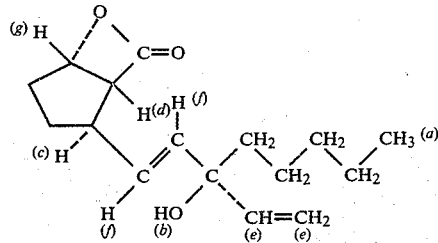

EXAMPLE 13 lactone of (1RS, 2SR, 5RS, 3'SR)(1'E) 2-hydroxy-5-(3'-acetoxy-1'-octenyl)-cyclopentane carboxylic acid A mixture of 0.2 g of the lactone of (1RS, 2SR, 5RS, 3'SR)(1'E) 2-hydroxy-5-(3'α-hydroxy-1'-octenyl)-cyclopentane carboxylic acid, 2 ml of methylene chloride, 0.47 ml of triethylamine, 0.091 ml of acetic acid anhydride and a few grains of dimethylamino-pyridine was stirred at room temperature for 2 hours and 3 ml of water were then added. The mixture was acidified to a pH of 5 with monosodium phosphate and was extracted with methylene chloride. The organic extracts were dried and evaporated to dryness under reduced pressure to obtain 266 mg of a raw oil. The latter was chromatographed over silica gel and was eluted with a 6-4 cyclohexane-ethyl acetate mixture to obtain 211 mg of the pure lactone of (1RS, 2SR, 5RS, 3'SR)(1'E) 2-hydroxy-5-(3'-acetoxy-1'-octenyl)-cyclopentane carboxylic acid with an RF=0.5.

IR Spectrum: complexed carbonyl at 1808 to 1824 cm$^{-1}$ and ester at 1725 cm$^{-1}$.

RMN Spectrum (CDCl$_3$ 60 MHz); (a) 0.88 ppm; (b) 2.03 ppm; (c) triplet centered at 3.08 ppm J=5 Hz; (d) doublet centered at 3.78 ppm J=3.5 Hz; (e) triplet centered against 5.01 ppm J=3 Hz and; (f) 5.15 ppm.

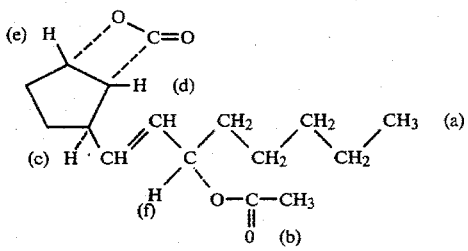

EXAMPLE 14

Hemisuccinate of the lactone of (1RS, 2SR, 5RS, 3'SR)(1'E) 2-hydroxy-5-(3'-hydroxy-1'-octenyl)-cyclopentane carboxylic acid A mixture of 119 mg of the lactone of (1RS, 2SR, 5RS, 3'-SR)(1'E) 2-hydroxy-5-(3'α-hydroxy-1'-octenyl)-cyclopentane carboxylic acid, 2 ml of anhydrous methylene chloride, 100 mg of succinic acid anhydride, 0.15 ml of pure triethylamine and 15 mg of 4-dimethylamino pyridine was refluxed for 8 hours and was then evaporated to dryness. 2 ml of absolute ethanol were added thereto and the mixture stood for an hour at room temperature. Excess succinic acid anhydride was removed as ethyl hemisuccinate and the mixture was evaporated to dryness under reduced pressure to obtain 226 mg of raw product. The latter was chromatographed over silica gel and was eluted with pure ethyl acetate to obtain 132 mg of pure hemisuccinate of the lactone of (1RS, 2SR, 5RS, 3'SR)(1'E) 2-hydroxy-5-(3'-hydroxy-1'-octenyl)-cyclopentane carboxylic and with an Rf=0.3.

RMN Spectrum (CDCl$_3$ 60 MHz): (a) 0.88 ppm; (b) 2.63 ppm; (c) 3.08 ppm; (d) 5.2 ppm; (e) 5.04 ppm; and (f) 5.33 to 5.58 ppm.

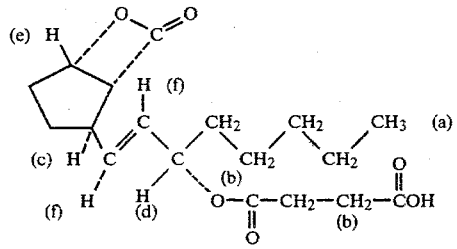

EXAMPLE 15 lactone of (1RS, 2SR, 5RS, 3'SR)(1'E) 2-hydroxy-5-(3'-hydroxy-1'-decenyl)-cyclopentane carboxylic acid STEP A: 1,2-epoxy-3α-tetrahydropyranyloxy-propane A solution of 3.9 g of glycol, 18.5 ml of dihydropyran and 150 mg of p-toluene sulfonic acid was heated at 40° C. for 30 minutes and then another 150 mg of p-toluene sulfonic acid were added thereto. After 15 minutes, the mixture was neutralized at room temperature with potassium carbonate and was then filtered. The filtrate was washed with ethyl acetate and evaporated to dryness under reduced pressure to obtain 8.48 g of 1,2-epoxy-3α-tetrahydropyranyloxy-propane with an Rf=0.6 (8-2 cyclohexane-ethyl acetate).

STEP B: methyl 3-oxo-6-hydroxy-7α-tetrahydropyranyloxyheptanoate

A suspension of 3.554 g of a 50% sodium hydride in oil and 16 ml of anhydrous tetrahydrofuran was added over 30 minutes to a solution of 8 ml of methyl acetylacetate and 16 ml of anhydrous tetrahydrofuran maintained at 0° C. and then 39 ml of butyllithium were added thereto over 30 minutes at 0° C. The mixture was stirred for 30 minutes and was then cooled to −70° C. The resulting solution was added over 45 minutes at 0° C. to a solution of 5.8 g of 1,2-epoxy-3α-tetrahydropyranyloxy-propane and 16 ml of tetrahydrofuran and the mixture was stirred for 3½ hours. The mixture was poured into an excess of a concentrated and iced solution of monosodium phosphate and was stirred for 10 minutes. The mixture was then extracted with ethyl acetate and the organic phase was washed with water until the wash waters were neutral and was evaporated to dryness to obtain 16.9 g of an oil. The latter was chromatographed over silica gel and was eluted with a 6-4 cyclohexane-ethyl acetate mixture to obtain 8.02 g of the pure methyl 3-oxo-6-hydroxy-7α-tetrahydropyranyloxyheptanoate with an Rf=0.15.

STEP C: methyl 3,6-dioxo-7α-tetrahydropyranyloxy-heptanoate 6 g of chromic acid were slowly added to a solution of 9.7 ml of pyridine in 148 ml of methylene chloride and after stirring the mixture for 15 minutes, a solution of 1.1 g of the product of Step B in 10 ml of methylene chloride was added thereto. After 15 minutes, 150 ml of ether were added thereto and the mixture was filtered. The filtrate was washed with ether and was evaporated to dryness to obtain 1.3 g of raw product. The latter was chromatographed over silica gel and was eluted with a 8-2 methylene chloride-ethyl acetate mixture to obtain 473 mg of methyl 3,6-dioxo-7α-tetrahydropyranyloxy-heptanoate with an Rf=0.45.

STEP D: methyl-2-(α-tetrahydropyranyloxy-methyl)-5-oxo-1-cyclopentene carboxylate A mixture of 291 mg of potassium bicarbonate, 72 ml of distilled water, 220 mg of the raw product of Step C and 2.4 ml of methylene chloride was vigorously stirred for 30 minutes and the mixture was acidified to a pH of with oxalic acid. The mixture was saturated with sodium chloride and was extracted with methylene chloride. The extracts were evaporated to dryness to obtain 205 mg of methyl 2-(α-tetrahydropyranyloxy methyl)-5-oxo-1-cyclopentene carboxylate.

STEP E: methyl (1RS, 5SR)-2-oxo-5-(α-tetrahydropyranyloxy methyl)cyclopentene carboxylate A solution of 215 mg of the product of Step D, 10 ml of methanol and 21 mg of carbon containing 10% palladium was stirred under a hydrogen atmosphere for 40 minutes during which the theoretical volume of hydrogen was absorbed and the mixture was filtered. The filtrate was washed with ethyl acetate and was evaporated to dryness to obtain 172 mg of an oil. The latter was chromatographed over silica gel and was eluted with a 1-1 cyclohexane-ethyl acetate mixture to obtain 122 mg of methyl (1RS, 5SR) 2-oxo-5-(α-tetrahydropyranyloxy methyl)-cyclopentane carboxylate.

STEP F: methyl (1RS, 5SR), 2-oxo-5-hydroxymethyl cyclopentane carboxylate

A mixture of 43 g of the product of Step E, 860 ml of methanol, 86 ml of water and 12.7 g of oxalic acid was stirred at 60° C. for 3 hours and was then concentrated to dryness under reduced pressure. The residue was taken up in chloroform and the solution was washed with water, and dried and evaporated to dryness to obtain 29.2 of raw product. The latter was chromatographed over silica gel and was eluted with an 8-2 ethyl acetate-cyclohexane mixture to obtain 14 g of pure methyl (1RS, 5SR) 2-oxo-5-hydroxymethyl cyclopentane carboxylate in the form of an oil.

STEP G: methyl (5RS) 2-methoxy-5-hydroxymethyl-1-cyclopentene carboxylate

A mixture of 4 g of the product of Step F, 10 ml of methylene chloride and 50 ml of a solution of diazomethane in methylene chloride was stirred for 4 hours at room temperature and the solvent and excess diazomethane were removed to obtain 4.3 g of raw methyl(5RS) 2-methoxy-5-hydroxymethyl-1-cyclopentene carboxylate in the form of a yellow oil which was used as is for the next step.

STEP H: methyl (5RS) 2-methoxy-5-formyl-1-cyclopentene carboxylate 25.5 g of chromic oxide were added in small fractions at 15° to 20° C. to a solution of 41 ml of pyridine in 400 ml of anhydrous methylene chloride and the mixture was stirred for 15 minutes and was then cooled to −15° C. A solution of 4.3 g of the product of Step G in 10 ml of methylene chloride was added thereto and after 90 minutes, 50 g of celite and 100 ml of ether were added. The mixture was filtered and the filtrate was washed with ether and evaporated to dryness at 30° C. to obtain methyl (5RS) 2-methoxy-5-formyl-1-cyclopentene-carboxylate.

STEP I: methyl (5RS)(1'E) 2-methoxy-5-(3'-oxo-1'-decenyl)-1-cyclopentene carboxylate A solution of 9.674 g of dimethyl (2-oxo-nonyl) phosphonate in 20 ml of glyme was added over 10 minutes to a suspension of 1.85 g of sodium hydride in 50% oil and after coagulation of the mass, a solution of 5 g of the product of Step H in 30 ml of glyme were added over 20 minutes. After a total reaction time of 20 minutes, the mixture was poured into an aqueous solution saturated with monosodium phosphate and the mixture was extracted with ethyl acetate to obtain 13.2 g of an oil. The latter was chromatographed over silica gel and was eluted with 6-4 cyclohexane-ethyl acetate mixture containing 1% by weight of triethylamine to obtain 4.652 g of methyl (5RS)(1'E) 2-methoxy-5-(3'-oxo-1'-decenyl)-1-cyclopentene carboxylate in the form of an oil with a Rf=0.25.

IR Spectrum: maximum at 1651 cm$^{-1}$ (carbonyl) and 1623 cm$^{-1}$ (conjugated C=C).

STEP J: methyl (5RS, 3'SR)(1'E) 2-methoxy-5-(3'-hydroxy-1'-decenyl)-1-cyclopentene carboxylate and methyl (5RS, 3'RS)(1'E) 2-methoxy-5-(3'-hydroxy-1'-decenyl)-1-cyclopentene carboxylate 200 ml of a solution of 0.13 M of zinc borohydride in glyme were added over 45 minutes at 0° C. to a solution of 4.6 g of the product of Step I in 100 ml of glyme distilled over sodium and after the temperature returned to room temperature, the mixture was stirred for 4 hours and was then poured into an aqueous solution saturated with monosodium phosphate. The mixture was extracted with ethyl acetate and the extracts were treated to obtain 7.3 g of an oil. The latter was subjected twice to chromatography over silica gel and was eluted with a 60-40 benzene-ethyl acetate mixture containing 1% by weight of triethylamine to obtain 901 mg of methyl (5RS, 3'SR)(1'E) 2-methoxy-5-(3'-hydroxy-1'-decenyl)-1-cyclopentene carboxylate and 810 mg of methyl (5RS, 3'RS) (1'E) 2methoxy-5-(3'-hydroxy-1'-decenyl)-1-cyclopentene carboxylate as well as 503 ml of a mixture of the said products.

STEP K: (1RS, 2SR, 5RS, 3'SR)(1'E) 2-hydroxy-5-(3'-hydroxy-1'-decenyl)-cyclopentane carboxylic acid A solution of 8.49 mg of the 3'SR isomer of Step J in 3 ml of methanol and 2 ml of 0.1 N hydrochloric acid was stirred for 15 hours at room temperature and the solution was then neutralized with 2 ml of 0.1 N sodium hydroxide. The aqueous phase was extracted with ether to obtain 763 mg of an oil with an Rf=0.32 (60-40 benzene-ethyl acetate). The 763 mg of oil was dissolved in 4 ml of tetrahydrofuran and the solution was added at 60° C. to 5.14 ml of a molar solution of selectride L in tetrahydrofuran. The mixture was stirred for 2½ hours at 60° C. and was then poured into an aqueous solution saturated with monosodium phosphate. The mixture was extracted with ethyl acetate to obtain 1.7 g of raw oil with an Rf=0.25 (40–60 cyclohexane-ethyl acetate).

A mixture of the said oil in 3 ml of ethanol and 2.4 ml of N sodium hydroxide was stirred for 2 hours and the ethanol was evaporated. The mixture was extracted with ethyl acetate and the aqueous phase was acidified to a pH of 5 with monosodium phosphate. The mixture was extracted with ethyl acetate and the organic phase was washed with water, dried and evaporated to dryness under reduced pressure to obtain 365 mg of a colorless oil after chromatography which was (1RS, 2SR, 5RS, 3'SR)(1'E) 2-hydroxy-5-(3'-hydroxy-1'-decenyl)-cyclopentane carboxylic acid with Rf=0.1 and 0.36 (ethyl acetate)

RMN Spectrum (CDCl$_3$ 60 MHz): (a) 0.88 ppm; (b) doublets centered at 2.4 and 2.59 ppm (J=5 Hz); (c) 4.06 ppm and (d) 4.5 ppm.

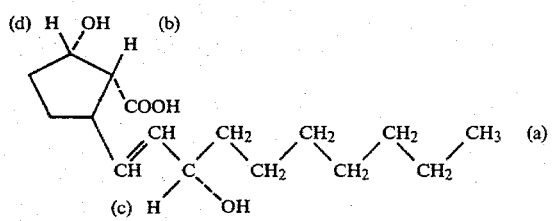

STEP L: lactone of (1RS, 2SR, 5SR, 3'SR)(1'E) 2hydroxy-5-(3'-hydroxy-1'-decenyl)-cyclopentane carboxylic acid A mixture of 0.15 g of (1RS, 2SR, 5RS, 3'SR)(1'E) 2-hydroxy-5-(3'-hydroxy-1'-decenyl)-cyclopentene carboxylic acid, 4 ml of chloroform, 0.315 g of triethylenediamine and 0.16 g of tosyl chloride instantly reacted and was then poured into water. The mixture was extracted with ethyl acetate and the extracts were treated to obtain 183 mg of an oil which was chromatographed over silica gel. Elution with a 6-4 cyclohexane-ethyl acetate mixture yielded 41 mg of the pure lactone of (1RS, 2SR, 5RS, 3'SR)(1'E) 2-hydroxy-5-(3'-hydroxy-1'-decenyl) cyclopentane carboxylic acid with an Rf=0.25.

IR Spectrum: complexed carbonyl at 1808 to 1824 cm$^{-1}$ and C=C at 973 cm$^{-1}$.

RMN Spectrum (CDCl$_3$ 60 MHz): (a) 0.88 ppm; (b) 1.3 ppm; (c) 1.53 ppm; (d) 3.08 ppm; (e) 3.78 ppm (doublet J=4 Hz); 4.05 ppm; (g) 5.47 ppm (doublet J=5 Hz); (h) 5.01 ppm (triplet).

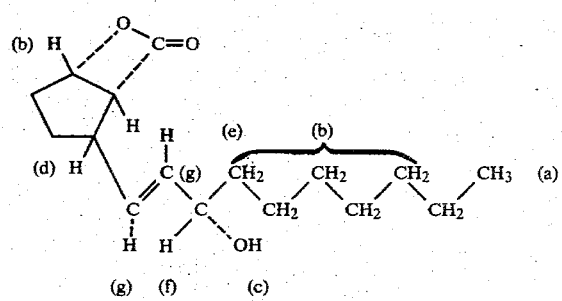

EXAMPLE 16

Lactone of (1RS, 2SR, 5RS, 3'SR)(1'E) 2-hydroxy-5-(3'α-hydroxy-1'-octenyl)-cyclopentane carboxylic acid Using the procedure of Example 1, the lactone of (1RS, 2SR, 5RS, 3'SR)(1'E) 2-hydroxy-5-(3'α-tetrahydropyranyloxy-1'-octenyl)-cyclopentane carboxylic acid with triethylamine being replaced by diazobicyclooctane was obtained which was treated as in Example 2 to obtain the lactone of (1RS, 2SR, 5RS, 3'SR)(1'E) 2-hydroxy-5-(3'α-hydroxy-1'-octenyl)-cyclopentane carboxylic acid.

EXAMPLE 17

Lactone of (1RS, 2SR, 5RS, 3'RS)(1'E) 2,3'-dihydroxy-5(1'-octenyl)-cyclopentane-carboxylic acid STEP A: Mixture of ethyl (1RS, 2SR, 5RS, 3'RS)(1'E) 2,3'-dihydroxy-5-(1'-octenyl)-cyclopentane carboxylate and ethyl (1RS, 2SR, 5RS, 3'SR)(1'E) 2,3'-dihydroxy 5-(1'-octenyl)-cyclopentane carboxylate.

A solution of 1.18 g of ethyl (1RS, 2SR, 5RS)(1'E) 2-hydroxy-5-(3'-oxo-1'-octenyl)-cyclopentane carboxylate in 30 ml of anhydrous glyme was maintained at 0° C. under inert atmosphere and then 34 ml of a 0.15 N solution of zinc borohydride in anhydrous glyme was added thereto dropwise at 0° C. A little later 20 ml and then 5 ml of the zinc borohydride solution were added thereto. The mixture was then poured into an iced aqueous solution saturated with monosodium phosphate, extracted with ethyl acetate, washed with water, dried over magnesium sulfate and evaporated the solvents under reduced pressure. The residue was chromatographed over silica gel and was eluted with a (1-1)cyclohexane-ethyl acetate mixture to obtain 471 mg of a mixture of ethyl (1RS, 2SR, 5RS, 3'RS)(1'E) 2,3'-dihydroxy-5-(1'-octenyl)-cyclopentane carboxylate and ethyl (1RS, 2SR, 5RS, 3'SR) (1'E) 2,3'-dihydroxy-5-(1'-octenyl)-cyclopentane carboxylate.

I.R. Spectrum (chloroform): hydroxyl at 3608 cm$^{-1}$, carboxyl at 1706 cm$^{-1}$ and 1727 cm$^{-1}$ (shoulder) and C=C at 970 cm$^{-1}$.

RMN Spectrum (CDCl$_3$ 60 MHz): (a) 1.28 ppm (triplet J=7 Hz); (b) 4.21 ppm (quadruplet J=7 Hz); (c) 2.37–2.56 ppm (2 doublets J=5 Hz); (d) ~4.42 ppm; (e) 5.58 ppm (doublet J=10 Hz); (f) 4.08 ppm (g) ~0.90 ppm.

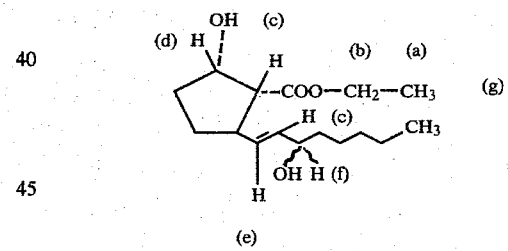

STEP B: (1RS, 2SR, 5RS, 3'RS)(1'E) 2,3'-dihydroxy-5-(1'-octenyl)-cyclopentane carboxylic acid A mixture of 426 mg of ethyl (1RS, 2SR, 5RS, 3'RS)(1'E) 2,3'-dihydroxy-5-(1'-octenyl)-cyclopentane carboxylate and ethyl (1RS, 2SR, 5RS, 3'SR)(1'E) 2,3'-dihydroxy-5-(1'-octenyl)-cyclopentane carboxylate was introduced into a solution of 8 ml of dioxane and 5.9 ml of 1 N sodium hydroxide. The mixture was maintained for two hours at room temperature under inert atmosphere and was then acidified by addition of hydrochloric acid and extracted with ethyl acetate. The organic phase was washed with aqueous sodium chloride and the solvents were evaporated under reduced pressure. The residue was chromatographed over silica gel and was eluted with a chloroform-methanol-acetic acid (90-10-1) mixture to obtain 348 mg of a mixture of the two isomers of 3'RS and 3'SR of the (1RS, 2SR, 5RS)(1'E) 2,3'-dihydroxy-5(1'-octenyl)-cyclopentane carboxylic acid. The latter was subjected to chromatography over silica gel and was eluted with a chloroform-methanol-acetic acid (90-10-1) mixture to obtain 106 mg of (1RS, 2SR, 5RS, 3'RS)(1'E) 2,3'-dihydroxy-5-(1'-octenyl)-cyclopentane carboxylic acid (Rf=0.26) and 64 mg of (1RS, 2SR, 5RS, 3'SR)(1'E) 2,3'-dihydroxy-5-(1'-octenyl)-cyclopentane carboxylic acid (RF=0.3).

STEP C: Lactone of (1RS, 2SR, 5RS, 3'RS)(1'E) 2,3'-dihydroxy-5-(1'-octenyl)-cyclopentane carboxylic acid A mixture of 106 mg of (1RS, 2SR, 5RS, 3'RS)(1'E) 2,3'-dihydroxy-5-(1'-octenyl)-cyclopentane carboxylic acid in 4 ml of anhydrous chloroform was admixed under an inert atmosphere at room temperature with 182 mg of diazabicyclooctane and 95 mg of tosyl chloride. The reaction mixture was stirred for 75 minutes at room temperature, then was added to 5 ml of an iced aqueous solution saturated with monosodium phosphate and was extracted with chloroform. The organic phases were washed with water, dried over magnesium sulfate, filtered and evaporated to dryness under reduced pressure. The oil residue was chromatographed over silica gel and was eluted with a (60-40) cyclohexane-ethyl acetate mixture to obtain 52.9 mg of the lactone of (1RS, 2SR, 5RS, 3'RS)(1'E) 2,3'-dihydroxy-5-(1'-octenyl)-cyclopentane carboxylic acid.

I.R. Spectrum (chloroform): carbonyl at 1809 cm$^{-1}$ to 1826 cm$^{-1}$(β-lactone), hydroxyl at 3606 cm$^{-1}$ and C=C at 968 cm$^{-1}$.

RMN Spectrum (CDCl$_3$-60 MHz); (a) ~0.88 ppm; (b) 3.82 ppm (doublet J=3.5 Hz); (c) 5.03 ppm (triplet J=3.5 Hz); (d) ~3.1 ppm; (e) ~5.5 ppm (ethylenic) (f) ~4.08 ppm.

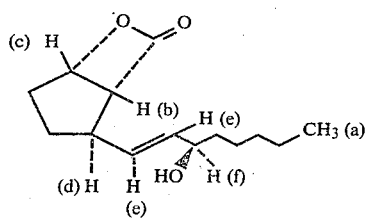

EXAMPLE 18

Lactone of (1RS, 2SR, 5RS, 3'SR)(1'E) 2-hydroxy-5-(3'-α-tetrahydropyranyloxy-1'-nonenyl)-cyclopentane carboxylic acid STEP A: Dimethyl 2-oxo-octanylphosphonate 115 ml of a 0.87 N solution of butyllithium in hexane were introduced in 30 minutes into a −10° C. solution of 12.4 g of dimethyl methylphosphonate and of 100 ml of anhydrous tetrahydrofuran. The reaction mixture was stirred for two hours at −10° C. and added over one hour to a solution of 15.8 g of ethyl heptanoate in 80 ml of anhydrous tetrahydrofuran. The reaction mixture was stirred again for two hours at −10° C. and returned to room temperature. The mixture was then poured into a saturated monosodium phosphate solution, extracted with ethyl acetate, dried over magnesium sulfate and evaporated to dryness. The residue was chromatographed over silica gel and eluted with an ethyl acetate-methanol mixture (96-4) to obtain 12.23 g of dimethyl 2-oxo-octanyl phosphonate (Rf=0.32).

I.R. Spectrum (chloroform):

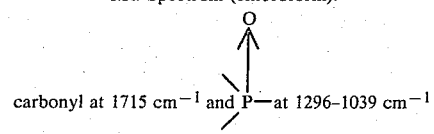

carbonyl at 1715 cm$^{-1}$ and P— at 1296-1039 cm$^{-1}$

STEP B: Methyl (5RS)(1'E) 2-methoxy-5-(3'-oxo-1'-nonenyl)-1-cyclopentene carboxylate A solution of 7.2 g of dimethyl 2-oxooctanyl-phosphonate in 20 ml of anhydrous glyme was introduced into a suspension of 1.455 g of sodium hydride as 50% in oil and 200 ml of glyme. The mixture was stirred for 1 hour and added over 20 minutes to 4.34 g of methyl (5RS) 2-methoxy-5-formyl-1-cyclopentane carboxylate in solution into 30 ml of anhydrous glyme. The mixture was left for 20 minutes, poured in an iced saturated monosodium phosphate solution, extracted with ethyl acetate, washed with water and evaporated to dryness under reduced pressure. The residue was chromatographed over silica gel and was eluted with a hexane-ethylacetate (60-40) mixture to obtain 2.05 g of methyl (5RS)(1'E) 2-methoxy-5-(3'-oxo-1'-nonenyl)-1-cyclopentene carboxylate (Rf=0.16).

I.R. Spectrum (chloroform): carbonyl at 1691 cm$^{-1}$ and C=C at 1623 cm$^{-1}$.

RMN Spectrum (CDCl$_3$—60 MHz): (a) 0.88 ppm (multiplet); (b) 3.7 ppm; (c) 3.88 ppm; (d) 3.92 ppm (doublet J=10 Hz); (e) 6.1 ppm (doublet J=16 Hz); (f) 6.71 ppm-6.97 ppm (2 doublets J=7 Hz).

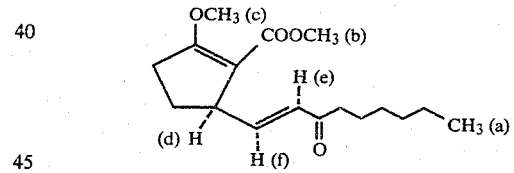

STEP C: Methyl (5RS, 3'SR)(1'E) 2-methoxy-5-(3'-hydroxy-1'-nonenyl)-1-cyclopentene carboxylate 22.6 ml of a solution of 0.8 M zinc borohydride in glyme were added dropwise at 0° C. into a solution of 2 g of methyl (5RS)(1'E) 2-methoxy-5-(3'-oxo-1'-nonenyl)-1-cyclopentene carboxylate and 50 ml of anhydrous glyme. The reaction mixture was maintained at 0° C. and stirred for two hours and was poured into a saturated monosodium phosphate solution. The mixture was extracted with ethyl acetate and the organic phases were washed with water and evaporated to dryness under reduced pressure. The residue was chromatographed over silica gel and was eluted with a (60-40) benzene-ethyl acetate mixture to obtain 522 mg of methyl (5RS, 3'SR)(1'E) 2-methoxy-5-(3'-hydroxy-1'-nonenyl)-1-cyclopentene carboxylate (Rf=0.18) 402 mg of the corresponding 3'RS isomer and 79 mg of a mixture of 3'SR and 3'RS isomers were also obtained.

STEP D: Methyl (1RS, 5RS, 3'SR)(1'E) 2-oxo-5-(3'-α-tetrahydropyranyloxy-1'-nonenyl)-cyclopentane-carboxylate A mixture of 522 mg of methyl (5RS, 3'SR)(1'E) 2-methoxy-5-(3'-hydroxy-1'-nonenyl)-1-cyclopentene-carboxylate, 3 ml of methanol and 1.7 ml of 0.1 N hydrochloric acid was stirred for 22 hours at room temperature and then was admixed with 1 ml of 0.1 N sodium hydroxide. The solvent was evaporated under reduced pressure and the residue was taken up in water and then extracted with ethyl acetate. The organic phases were washed with water, dried over magnesium sulfate and evaporated to dryness under reduced pressure to obtain 458 mg of methyl (1RS, 5RS, 3'SR)(1'E) 2-oxo-5-(3'-hydroxy-1'-nonenyl)-cyclopentane carboxylate.

The 458 mg of the above mentioned compound were introduced into a mixture of 7 ml of ether, 1.8 ml of dihydropyrane and 6 mg of paratoluenesulfonic acid and the mixture was stirred for 1 hour. Sodium carbonate was added thereto and the mixture was stirred again for 30 minutes. The mixture was filtered and the filtrate was washed with ether and evaporated under reduced pressure. The residue was chromatographed over silica gel and was eluted with a cyclohexane-ethyl acetate mixture (70–30) to obtain 482 mg of methyl (1RS, 5RS, 3'SR)(1'E) 2-oxo-5-(3'-α-tetrahydropyranyloxy-1'-nonenyl)-cyclopentane carboxylate (Rf=0.17).

STEP E: (1RS, 2SR, 5RS, 3'SR)(1'E) 2-hydroxy-5-(3'-α-tetrahydropyranyloxy-1'-nonenyl)-cyclopentane-carboxylic acid A solution of 482 mg of methyl (1RS, 5RS, 3'SR)(1'E) 2-oxo-5-(3'-α-tetrahydropyranyloxy-1'-nonenyl)-cyclopentane carboxylate in 3 ml of tetrahydrofuran was introduced dropwise into 3 ml of a molar solution of L-selectride in tetrahydrofuran. The mixture was stirred for two hours and then was poured into an aqueous solution saturated with monosodium phosphate. The mixture was extracted with ethyl acetate and the organic phases were washed with water, dried and evaporated to dryness to obtain 793 mg of methyl (1RS, 2SR, 5RS, 3'SR)(1'E) 2-hydroxy-5-(3'-α-tetrahydropyranyl-1'-nonenyl)-cyclopentane-carboxylate. A mixture of the 793 mg of the above mentioned compound, 3 ml of methanol and 4 ml of 1 N sodium hydroxide was stirred at room temperature for 7 hours. The solvent was evaporated under reduced pressure and the residue was taken up with water and ethyl acetate and the solution was decanted. The aqueous phase was acidified with monosodium phosphate, extracted with ethyl acetate and evaporated to dryness under reduced pressure to obtain 300 mg of (1RS, 2SR, 5RS, 3'SR) (1'E) 2-hydroxy-5-(3'-α-tetrahydropyranyloxy-1'-nonenyl)-cyclopentane carboxylic acid.

STEP F: Lactone of (1RS, 2SR, 5RS, 3'SR)(1'E) 2-hydroxy-5-(3'-α-tetrahydropyranyloxy-1'-nonenyl)-cyclopentane carboxylic acid 257 mg of tosyl chloride were introduced in 3 portions into a solution containing 300 mg of (1RS, 2SR, 5RS, 3'SR) (1'E) 2-hydroxy-5-(3'-α-tetrahydropyranyloxy-1'-nonenyl)-cyclopentane carboxylic acid, 8 ml of anhydrous chloroform and 503 mg of diazobicyclooctane and the reaction mixture was poured into a saturated solution of monosodium phosphate and was extracted with ethyl-acetate. 321 mg of a raw product were obtained and purified over silica gel to obtain 212 mg of the lactone of (1RS, 2SR, 5RS, 3'SR)(1'E) 2-hydroxy-5-(3'-α-tetrahydropyranyloxy-1'-nonenyl)-cyclopentane carboxylic acid.

EXAMPLE 19

Lactone of (1RS, 2SR, 5RS, 3'SR)(1'E) 2,3'-dihydroxy-5-(1'-nonenyl)-cyclopentane carboxylic acid A mixture of 212 mg of the lactone of (1RS, 2SR, 5RS, 3'SR)(1'E) 2-hydroxy-5-(3'-α-tetrahydropyranyloxy-1'-nonenyl)-cyclopentane carboxylic acid (of Example 18), 2.5 ml of ethanol, 1.25 ml of water and 50 mg of oxalic acid was stirred for 3 hours at 50° C. and was then evaporated to dryness under reduced pressure. The residue was taken up in chloroform and the mixture was filtered and evaporated to dryness to obtain 167 mg of raw product. The latter was chromatographed over silica gel and was eluted with a cyclohexane-ethyl acetate mixture (60–40) to obtain 67 mg of the lactone of (1RS, 2SR, 5RS, 3'SR)(1'E) 2,3'-dihydroxy-5-(1'-nonenyl)-cyclopentane carboxylic acid.

I.R. Spectrum (chloroform): carbonyl at 1827 cm$^{-1}$ (shoulder toward 1815 cm$^{-1}$) hydroxy at 3600 cm$^{-1}$.

RMN Spectrum (CDCl$_3$—60 MHz): (a) 0.88 ppm; (b) 3.81 ppm (double J=4 Hz); (c) 5.03 ppm; (d) 3.09 ppm; (e) 5.48 ppm; (f) 4.06 ppm.

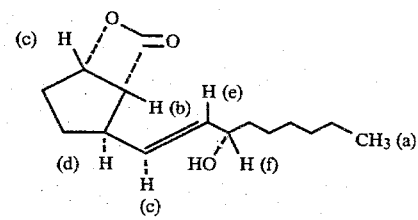

PHARMACOLOGICAL DATA

The products used in the following tests were the lactone of (1RS, 2SR, 5RS, 3'SR)(1'E) 2-hydroxy-5-(3'-hydroxy-1'-octenyl)-cyclopentane carboxylic acid [product A], the lactone of (1RS, 2SR, 5RS, 3'RS)(1'E) 2-hydroxy-5-(3'-hydroxy-3'-ethynyl-1'-octenyl)-cyclopentane carboxylic acid [product B], the lactone of (1RS, 2SR, 5RS, 3'RS)(1'E) 2-hydroxy-5-(3'-hydroxy-3'-ethenyl-1'-octenyl)-cyclopentane carboxylic acid [product C], the lactone of (1RS, 2SR, 5RS, 3'SR)(1'E) 2-hydroxy-5-(3'-acetoxy-1'-octenyl)-cyclopentane carboxylic acid [product D], the lactone of (1RS, 2SR, 5RS, 3'SR)(1'E) 2-hydroxy-5-(3'-hydroxy-1'-decenyl)-cyclopentane carboxylic acid [product E], the lactone of (1RS, 2SR, 5RS, 3'RS)(1'E) 2,3'-dihydroxy-5-(1'-octenyl)-cyclopentane carboxylic acid [product F] and the lactone of (1RS, 2SR, 5RS, 3'SR)(1'E) 2,3'-dihydroxy-5-(1'-nonenyl)-cyclopentane carboxylic acid [product G].

A. Hypotensive Activity in Anesthesized dogs

The test used bastard adult dogs of both sexes weighing 14 to 20 kg with a closed thorax and the dogs were anesthesized with chloralose at 125 mg/kg intraveinously. The trachea had a tube placed therein and the dogs were artifically ventilated with a pump. The arterial pressure was expressed in mm Hg taken on the carotide with the aid of a pressure gauge. The cardiovascular effects were determined by the average arterial pressure (diastolic pressure $+\frac{1}{3}$ of systolic pressure minus diastolic pressure) at doses of 10 to 1000γ/ kg intraveinously for product A and 30 to 1000γ/ kg for product B. The following Table indicates the maximum variation of the average arterial pressure as well as the time necessary for the pressure to return to the starting pressure.

TABLE I

| Dose in γ/kg | Product A | | Product B | |
|---|---|---|---|---|
| | % Average variation | duration in min. | % variation | duration in min. |
| 10 | −40 | 8 | — | — |
| 30 | −5 | 5 | 0 | — |
| 100 | −17 | 18 | 0 | — |
| 300 | −25 | 16.30 | −8 | 8.30 |
| 1000 | −31 | 37 | −17 | 20 |

The products showed an interesting hypotensive activity beginning at a dose of 0.1 mg/kg for product A and 1 mg/kg for product B.

A second test was effected on bastard adult dogs of both sexes-weighing between 14 and 20 kg with a closed thorax and they were anesthesized with a mixture of barbiturates. The trachae had a tube placed therein and the dogs were artifically ventilated with a pump. The arterial pressure was determined on the carotide with a pressure gauge to determine the dose which diminished the average arterial pressure by at least 20% for at least 20 minutes. These doses were 0.5 mg/kg for product C and 1 mg/kg for products D and E.

B. Hypotensive Activity in Rabbits

The products were administered intraveinously in solution in physiological serum containing 10% ethanol to rabbits anesthesized with urethane and the carotide pressure was determined. The dose which lowered the pressure by 30% was found to be 20 μg/kg for product E, 50 μg/kg for product C and 100 μg/kg for products F and G.

Various modifications of the products and methods of the invention may be made without departing from the spirit or scope thereof and it is to be understood that the invention is to be limited only as defined in the appended claims.

We claim:

1. A lactone of the formula

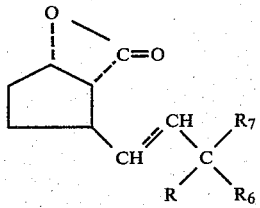

wherein the dotted line indicates the optional presence of a second bond, R is selected from the group consisting of hydrogen, alkyl of 1 to 4 carbon atoms and alkenyl and alkynyl of 2 to 4 carbon atoms, and R and $R_6$ together form a keto group, $R_7$ is $-(CH_2)_{m_A}-CH_3$, $m_A$ is 3,4,5 or 6 or $R_6$ and $R_7$ taken together form $=CH-(CH_2)_{n_A}-CH_3$, $n_A$ is 2,3,4, or 5.

2. A compound of claim 1 which is the lactone of (1RS, 2SR, 5RS)(1'E, 3'E) 2-hydroxy-5-(1',3'-octadienyl)-cyclopentane carboxylic acid.

3. An hypotensive composition comprising an hypotensively effective amount of a compound of claim 1 and an inert pharmaceutical carrier.

4. A composition of claim 3 wherein the active compound is (1RS, 2SR, 5RS)(1'E, 3'E) 2-hydroxy-5-(1',3'-octadienyl)-cyclopentane carboxylic acid.

5. A method of relieving hypertension and circulatory troubles in warm-blooded animals comprising administering to warm-blooded animals an hypotensively effective amount of a compound of claim 1.

6. The method of claim 5 wherein the active compound is (1RS, 2SR, 5RS)(1'E, 3'E) 2-hydroxy-5-(1',3'-octadienyl)-cyclopentane carboxylic acid.

* * * * *

UNITED STATES PATENT AND TRADEMARK OFFICE
CERTIFICATE OF CORRECTION

PATENT NO. : 4,279,919
DATED : July 21, 1981
INVENTOR(S) : JEAN BUENDIA and MICHEL VIVAT It is certified that error appears in the above—identified patent and that said Letters Patent is hereby corrected as shown below:

Column 8, line 20: "acd" should read -- acid --.

Column 18, line 27: "(1'E" should read -- (1'E) --.

Column 19, line 58: Delete "diluted" and insert instead -- dried --.

Column 24, line 9; Column 25, line 11: "RF" should read -- Rf --.

Column 26, line 8: "glycol should read -- glycidol --.

Column 26, line 23: "acety-" should read -- acetyl- --.

line 24: "lacetate" should read -- acetate --.

Column 28, line 32: "2methoxy" should read -- 2-methoxy --.

Column 29, line 12: "5 SR" should read -- 5 RS --.

line 13: "2hydroxy" should read -- 2-hydroxy --.

Signed and Sealed this

Twenty-fourth Day of November 1981

[SEAL]

Attest:

GERALD J. MOSSINGHOFF

Attesting Officer    Commissioner of Patents and Trademarks